United States Patent
Miller et al.

(10) Patent No.: US 10,456,792 B2
(45) Date of Patent: Oct. 29, 2019

(54) SINGLE, THIEF-SAMPLING, CALIBRATION AND CONTROL OF SEPARATOR APPARATUS AND METHOD

(71) Applicant: ECONOVA, INC., Clearfield, UT (US)

(72) Inventors: C. Michael Miller, Pleasant Grove, UT (US); D. Andrew Bell, Farmington, UT (US); Ngai Keung Tam, Farmington, UT (US)

(73) Assignee: THOUGHT PRESERUE, LLC

( * ) Notice: Subject to any disclaimer, the term of this patent is extended or adjusted under 35 U.S.C. 154(b) by 309 days.

(21) Appl. No.: 15/078,788

(22) Filed: Mar. 23, 2016

(65) Prior Publication Data
US 2016/0339452 A1   Nov. 24, 2016

Related U.S. Application Data

(60) Continuation-in-part of application No. 14/336,220, filed on Jul. 21, 2014, now Pat. No. 9,737,831, which
(Continued)

(51) Int. Cl.
*B04B 11/02* (2006.01)
*G01F 1/74* (2006.01)
(Continued)

(52) U.S. Cl.
CPC .......... *B04B 11/02* (2013.01); *B01D 17/0217* (2013.01); *B01D 17/12* (2013.01);
(Continued)

(58) Field of Classification Search
CPC ......... B04B 11/02; B04B 1/04; B04B 5/0442; B04B 13/00; B04B 1/12; B04B 2013/006;
(Continued)

(56) References Cited

U.S. PATENT DOCUMENTS 2,997,878 A * 8/1961 Graham ................ G01F 23/263
                                                                 174/112
3,410,480 A   11/1968 Fierstine
(Continued)

FOREIGN PATENT DOCUMENTS

WO   WO 2017105863 A1 * 6/2017 .............. C02F 1/008

OTHER PUBLICATIONS

Exterran, Deep Bad Nutshell Filter Evolution, p. 1-15, 2013.
(Continued)

*Primary Examiner* — Walter D. Griffin
*Assistant Examiner* — Shuyi S. Liu
(74) *Attorney, Agent, or Firm* — Pate Baird, PLLC

(57) ABSTRACT

A centrifugal, liquid-liquid separator is controlled, first by automatic control of back pressure to position of the dispersion band and equalize the settling lengths of both heavy and light phases. In line testing of a parameter reflecting the BS&W content of output oil controls withdrawal from a tank, and throughput rate through the separator. Output always meets a predetermined specification established on a daily basis by a market price and quality (contamination limit, maximum BS&W) for oil. Control provides assurance that all of a particular load in a tank will meet specification, and that it cannot change significantly before refining. Once the adjustment of the separator system reaches its lowest flow limit, processing halts, to assure that the oil quality is optimized. The controller may be used on any tank of separated oil to assure that no oil is withdrawn "out of spec."

19 Claims, 19 Drawing Sheets

Related U.S. Application Data is a division of application No. 14/104,970, filed on Dec. 12, 2013, now Pat. No. 9,527,012, said application No. 14/336,220 is a division of application No. 14/104,916, filed on Dec. 12, 2013, now Pat. No. 9,433,877.

(60) Provisional application No. 61/814,760, filed on Apr. 22, 2013.

(51) Int. Cl.
| | |
|---|---|
| G01F 1/88 | (2006.01) |
| G01N 27/22 | (2006.01) |
| B04B 1/12 | (2006.01) |
| B01D 17/12 | (2006.01) |
| B01D 17/02 | (2006.01) |
| B04B 1/04 | (2006.01) |
| B04B 5/04 | (2006.01) |
| B04B 13/00 | (2006.01) |
| C02F 1/38 | (2006.01) |
| C02F 1/00 | (2006.01) |
| C02F 101/32 | (2006.01) |
| C02F 103/10 | (2006.01) |

(52) U.S. Cl.
CPC ............... *B04B 1/04* (2013.01); *B04B 1/12* (2013.01); *B04B 5/0442* (2013.01); *B04B 13/00* (2013.01); *C02F 1/008* (2013.01); *C02F 1/38* (2013.01); *G01F 1/74* (2013.01); *G01F 1/88* (2013.01); *G01N 27/22* (2013.01); *B04B 2013/006* (2013.01); *C02F 2101/32* (2013.01); *C02F 2103/10* (2013.01); *C02F 2209/03* (2013.01); *C02F 2209/40* (2013.01); *C02F 2301/022* (2013.01)

(58) Field of Classification Search
CPC ........ C02F 1/008; C02F 1/38; C02F 2209/03; C02F 2209/40; C02F 2101/32; C02F 2301/022; C02F 2103/10; B01D 17/12; B01D 17/0217; G01F 1/74; G01F 1/88; G01N 27/22
USPC .............................................. 494/1, 3, 10, 37
See application file for complete search history.

(56) References Cited

U.S. PATENT DOCUMENTS

| | | | | |
|---|---|---|---|---|
| 3,602,033 | A | * | 8/1971 | Burrell .............. G01N 33/2823 73/1.02 |
| 3,804,333 | A | * | 4/1974 | Kramer .................... F23G 7/05 239/124 |
| 4,044,943 | A | | 8/1977 | Brown |
| 5,350,527 | A | * | 9/1994 | Kitko .................... B01D 17/02 210/109 |
| 5,948,271 | A | | 9/1999 | Wardwell et al. |
| 5,996,690 | A | * | 12/1999 | Shaw ..................... B04C 11/00 166/250.01 |
| 6,348,154 | B1 | | 2/2002 | Stewart |
| 6,860,845 | B1 | * | 3/2005 | Miller ...................... B04B 1/20 494/1 |
| 7,060,017 | B2 | | 6/2006 | Collier |
| 8,187,474 | B2 | | 5/2012 | Freeman |
| 2009/0204419 | A1 | | 8/2009 | Stewart |
| 2011/0003676 | A1 | | 1/2011 | Collier et al. |
| 2011/0263407 | A1 | * | 10/2011 | Jew ....................... C02F 11/127 494/6 |
| 2017/0174530 | A1 | * | 6/2017 | Yin ......................... C02F 1/008 |

OTHER PUBLICATIONS

McGraw Hill Higher Education, Unit Operations of Chemical Engineering, Seventh Edition, p. Chapter 2, p. 39-41, 2005.
Eastern Economy Edition, Transport Processes and Separation Process Principles, Christie John Geankoplis, Fourth Edition, p. 932-939, 2003.
John Wiley & Sons, Department of Chemical Engineering, R. Byron Bird, Warren E. Stewart, Edwin N. Lightfoot, Transport Phenomena, p. 85, 1960.
Wiley-India, Dale E. Seborg, Process Dynamics and Control, Second Edition, Thomas F. Edgar, Duncan A. Mellichamp, pp. 159-160 and p. 433-435, 2004.
McGraw Hill, Perry's Chemical Engineers' Handbook, Eighth Edition, Don W. Green, p. 18-114-116, 15-91-93, and 15-96-102, 2008.
High-Tech Consultants, Inc., Oilfield Water-Oil-Solids Separation, Bill Ball, Sep. 19, p. 1-17, 2005.
IOP Publishing, Nanostructured materials for water desalination, T. Humplik, J. Lee, S.C. O'her, B.A. Fellman, M.A. Baig, S.F. Hassan, M.A. Atich, F. Rahman, T. Laoui, R. Karnik, E.N. Wang, p. 1-19, 2011.

* cited by examiner $$|v| = \frac{2}{9}\frac{(\rho_p - \rho_f)}{\mu_f} gD^*_p{}^2 \quad \text{Equation 1}$$

Where:
$|v|$ is the settling velocity of an average droplet.
$\rho_p$ is the density of the droplet.
$\rho_f$ is the density of the fluid.
g is the gravitational force which is equal to $\omega^2 r$ in a centrifuge.
$D^*_p$ is the average radius of the droplets.
$\mu_f$ is the viscosity of the fluid.

FIG. 6

$$l_s = \tau \cdot |v| = \frac{V}{Q} \cdot |v| \quad \text{Equation 2}$$

Where:
$l_s$ is the settling length towards the interface.
$\tau$ is the residence time of the fluid in a centrifuge.
V is the volume capacity of the centrifuge.
Q is the flow rate of the fluid.

FIG. 7

$$\frac{Q_{heavy}}{Q_{total}} = \left[ (WVF_c(r_i) - 1) \left( \frac{r_i + r_2}{r_i} \right) \left( \frac{D_{light}}{D_{heavy}} \right)^2 \left( \frac{\mu_{light}}{\mu_{heavy}} \right) \right] + 1$$

Equation 3

Where:
$\omega$ is the angular velocity of the centrifuge.
$r_i$ is the radius of the interfacce .
$r_2$ is the radius at the end of the centrifuge .
$r_{light}$ is the average radius of the light phase, $r_{light} = r_i/2$ .
$r_{heavy}$ is the average radius of the heavy phase, $r_{heavy} = (r_i + r_2)/2$ .
$D_{light}$ is the diameter of a light phase droplet.
$D_{heavy}$ is the diameter of a heavy phase droplet.
$\mu_{light}$ is the viscosity of the light phase fluid.
$\mu_{heavy}$ is the viscosity of the heavy phase fluid.
$V_{light}$ is the volume capacity of the light phase of the centrifuge.
$V_{heavy}$ is the volume capacity of the heavy phase of the centrifuge.
$V_c$ is the volume of the centrifuge.
$Q_{light}$ is the flow rate of the separated light phase.
$Q_{heavy}$ is the flow rate of the separated heavy phase.
$Q_{influent}$ is the flow rate of the influent.
$l_s$, light is the settling length of the light phase.
$l_s$, heavy is the settling length of the heavy phase.
$|v|_{light}$ is the average settling velocity of the light droplet.
$|v|_{heavy}$ is the average settling velocity of the heavy droplet.

FIG. 8

$$WVF_c(r_i) = 1 - \frac{\pi L(r_i^2 - r_3^2)}{V_c} \quad \text{Equation 4a}$$

Where:
$WVF_c(r_i)$ is the water volume fraction of the centrifuge which is a function of $r_i$.

When:
$R_i \leq R_1$

FIG. 9A $$WVF_c(r_i) = \frac{\pi L}{3(R_2 - R_1)V_c}(2R_i^3 - 3R_i^2 R_2 + R_2^3)$$

Equation 4b

Where:
L is the length of the centrifuge.
$R_3$ is the radius of the shaft.
$R_1$ and $R_2$ are the radii of the centrifuge.

When:
$R_i > R_1$

FIG. 9B $$\Delta P = \frac{1}{2}\omega^2 [\rho_{heavy} * (R_i^2 - R_4^2) - \rho_{light} * (R_i^2)]$$

Equation 5

Where:
$\Delta P$ is the required additional pressure on the light phase.
$R_4$ is the minimum radius of the water effluent line.

FIG. 10

SINGLE, THIEF-SAMPLING, CALIBRATION AND CONTROL OF SEPARATOR APPARATUS AND METHOD

RELATED APPLICATIONS

This application: is a continuation in part of U.S. patent application Ser. No. 14/336,220, filed Jul. 21, 2014; which is a divisional (continuation) application of U.S. patent application Ser. No. 14/104,970, filed Dec. 12, 2013, which claims the benefit of U.S. Provisional patent application Ser. No. 61/814,760, filed Apr. 22, 2013; and is a divisional (continuation) application of U.S. patent application Ser. No. 14/104,916, filed Dec. 12, 2013, which claims the benefit of U.S. Provisional Patent Application Ser. No. 61/814,760, filed Apr. 22, 2013; all of which are hereby incorporated by reference. This application also hereby incorporates by reference U.S. Provisional patent application Ser. No. 62/208,945, filed Aug. 24, 2015 and U.S. Provisional patent application Ser. No. 62/259,856, filed Nov. 25, 2015. All the foregoing references are hereby incorporated herein by reference.

BACKGROUND

Field of the Invention

This invention relates to separators and, more particularly, to novel systems and methods for optimizing performance of liquid-liquid separators, and additionally is directed to a mechanism for feedback control of the output quality of oil from a centrifugal separator.

3. Background Art

Water purification is an activity required to meet various requirements. For example, waste water from industrial processes may require remediation before returning the basic water stream into a riparian flow, estuary, lake, sea, or other supply. Similarly, production water generated during production of petroleum, natural gas, or other petroleous materials may require remediation before disposal in any one of several ways.

For example, oil needs to be removed from water before it is re-injected into a disposal well. Otherwise, fouling will reduce the life of the disposal well. Similarly, if industrial contaminants or production water is re-injected into a disposal well, potential ground water contamination may be a consideration requiring removal of certain species of contaminants in the water.

On the other hand, production water may contain valuable oil that should be separated from the water for inclusion in the production of a well. Accordingly, water may be purified in order to separate out available petroleous product. By the same token, water separation from oil to a volume fraction of less than one percent or a mass fraction of less then one percent may be required to obtain optimum prices for crude oil.

Technologies have been developed for separating species of liquids of disparate phases (where each species is considered to be a separate phase, even within the same liquid state). U.S. Pat. No. 6,607,473, incorporated by reference herein; discloses certain embodiments of liquid-liquid separators.

As a practical matter, separation processes, specifically liquid-liquid separation processes, are a staple of chemical engineering practice. As a direct result, certain rules, formula, procedures, rules of thumb, and the like may typically be relied upon. Nevertheless, much of settling theory originates in static settling tanks or settling ponds. These are not actually static, but the pond or tank wall itself is static. The flow passes through as the effects of gravity on the differentials of buoyancy between constituents within the flow thereby separate them out, coalesce, or otherwise render them separable from one another.

In the chemical engineering arts, much of settling theory applied to stationary tanks has also been applied to the extent deemed appropriate to rotating separators, such as cylindrical tanks. Cylindrical tanks may have a fixed wall with a moving rotor inside. Other cylindrical tanks may actually rotate in their entirety.

However, prior art systems suffer from non-optimized operation. The controlling parameters to design them and scale them rely on conventional settling theory. The controlling parameters recognized are built into the very designs. They lack control variables effective to control and adjust operations with changing conditions "on the fly" during operation. They lack control systems and control mechanisms by which to control outputs by manipulation of control variables.

It is the conventional wisdom in settling systems to maximize the settling area of a settling tank. This means that the interface between the two principal species (phases) being separated from one another should have a maximum area. When one thinks of diffusion across a boundary, increased area in the diffusion equation suggests a higher total amount of diffused species. In other words, the total flux is increased when the rate of flux per unit area is multiplied by a larger, even the largest, available area. Thus, it is conventional wisdom that the surface area of the interface between the separating phases be maximized.

If a parameter changes, such as rotational velocity, pump throughput, constituents of the influent, fractions of influents, or the like, the interface radius between the separating phases simply finds its own new equilibrium position. There was no control of that interface. The control of the output of the separated phases was a result of the design parameters, and not manipulated by the operational parameters of the machine. It could be affected by the influents and by the temperature of the influent (which could be uncontrolled as a result of the environment, or could be controlled by adding heaters into the system), but the design was the design.

The '473 patent provided development of a mechanism to alter the set point of operation of a rotating separator. That mechanism was a recognition that the back pressure on the comparatively lighter phase being separated could modify the position (radius) of the surface of revolution, actually a the thin region of revolution, that constitutes the interface between the separating phases. Thus, an operator could specify the radius (radius of revolution of the dispersion band or interface) and maintain that position by altering the back pressure on the output or effluent line of the lighter phase.

That is, the understanding that back pressure could affect the radius of the dispersion band was developed in U.S. Pat. No. 6,607,473. However, the ability to determine what that radius should be (other than a "maximum area") has never been established to Applicants' knowledge in the prior art.

Moreover, no principal or mechanism has been developed for understanding the relationship between input variables (e.g., independent variables, properties, and the like of the incoming influent and the geometry of the separation device) as they may affect the desirable radius required of a dispersion band. Moreover, the relationship between the position of the dispersion band and the output properties has not been established, nor even the influence of the incoming input parameters thereon. Moreover, no mechanism for establishing control therebetween has been found in the prior art.

What are needed are mechanisms, operating principles, and even an understanding of the underlying phenomena and their parameters that may affect the material properties or behaviors of processed streams. Moreover, what is needed is a mechanism for understanding the effect of changes of those parameters. What would also advance the art are a system and apparatus as well as an operational method, even an experimental determination method, for determining and controlling the parameters on which the actual output depends.

For example, it is conventional wisdom, as discussed above, to maximize the area of the surface of rotation of the dispersion band in a rotating separator. However, experiments by Applicants demonstrate that this has a negative effect on the actual turbidity or purity of the output species. At present, it would be an advance in the art to find a principle and a mechanism whereby a previously selected quality of the output may be controlled by controlling any operational parameters within a separator after the time of design and construction. For example, it would be an advance in the art to provide any type of online quality control of the output by adjusting an operational parameter. This should be based on an understanding or measurement of the inputs, operational set points, or both.

It would also be an advance in the art to provide a principle and mechanism for determining an optimal location for the radius of the dispersion band (phase interface) within a separator. It would be a further advance in the art to provide a method and apparatus for optimizing any output parameter, such as purity, volumetric flow rate, efficiency, preferential purity of one species, or the like based on modifying internal parameters, and more particularly on the fly during operation.

BRIEF SUMMARY OF THE INVENTION

In view of the foregoing, in accordance with the invention as embodied and broadly described herein, a method and apparatus are disclosed in one embodiment of the present invention as including a system, apparatus, and method for controlling and optimizing the output of a rotating separator by monitoring various input parameters, adjusting automatically the radius of the dispersion band, and thereby giving a meaningful control algorithm to the control of back pressure.

Accordingly, in an apparatus and method in accordance with the invention, the phenomena have been studied, experimental data have been collected, relationships have been posited and established by experimental data, and a control scheme has been developed for optimizing the radius of a dispersion band and controlling it to optimize an output parameter characterizing the effluents from a rotating separator. The principle applies to separators in general. In one embodiment, a specific geometry is tested to demonstrate the general principles and the specific performance of that particular geometry.

In certain embodiments, an apparatus in accordance with the invention may include a separator operating to separate out at least one first liquid from at least one second liquid. It may be characterized by an inlet receiving a mixture of the at least one first liquid and the at least one second liquid and a dispersion band therein positioned between a bulk flow of the at least one first liquid and a bulk flow of the at least one second liquid.

The separator may include a first outlet discharging the at least one first liquid, and a second outlet discharging the at least one second liquid. A control system, operably connected to the separator, positions the dispersion band automatically, based on the cut of one of the at least one first liquid and the at least one second liquid. The cut is defined as the fraction that one of the first and second liquids represents out of the total flow on the incoming mixture.

The control system may include an inlet flow meter detecting an inlet flow rate of the mixture into the separator. A first outlet flow meter detects a flow rate of the at least one first liquid through the first outlet, while a second outlet flow meter detects a second flow rate of the at least one second liquid through the second outlet. The control system may be programmed to automatically adjust a pressure differential between the first outlet and the second outlet based on the cut of one phase or species of interest, a ratio of one of the first and second flow rates to the inlet flow rate.

The control system may have a first sensor sensing a first pressure proximate the first outlet, a second sensor sensing a second pressure proximate the second outlet, a comparator automatically reporting a differential between the first and second pressures, and a control valve automatically positioning the dispersion band by controlling the differential. The control system may be programmed to position the dispersion band at a location corresponding to equality between a first settling distance corresponding to droplets of the at least one second liquid migrating through the at least one first liquid and a second settling distance corresponding to droplets of the at least one first liquid migrating through the at least one second liquid.

The settling distance is a defined mathematical product of a settling velocity and a residence time corresponding to the separator. It applies to a droplet of one of the liquids traveling under the influence of buoyancy and drag forces, through the other liquid. Meanwhile, each bulk liquid corresponds to its own residence time, reflecting a bulk flow thereof from an inlet to an outlet.

In the experiments, the separator was a rotating separator. It was shaped as a frustum of a cone, having a tapered wall. The wall extends in an axial direction from an inlet end to an outlet end, progressing from a smaller diameter proximate the inlet end to a larger diameter proximate the outlet end.

The first liquid is measurably different in density from the second, and the more dense liquid of the two carries with it a flow of even heavier solid particles. Other solids of lower density could move to the opposite extreme, including remaining in the dispersion band, depending on their density. The system includes a computerized control, automatically controlling back pressure on the less dense of the first and second liquids based on optimizing separation quality at the cut value of a liquid of interest separating out from the influent.

The controller may include a processor, and may have its own dedicated computer that reports to and is programmed either directly, or from another system computer, or both. The controller computer provides values of settings to be consequently maintained by a comparator connected to first and second pressure sensors. The first pressure sensor senses a first pressure corresponding to the first outlet discharging the first liquid. The second pressure sensor senses a second pressure corresponding to the second outlet. The control system may be programmed (by programming the system computer, the controller computer, the comparator, or a combination thereof) to control a value of a pressure differential maintained between the first and second outlets and thus between their pressures.

A control system is thus programmed to establish for the comparator a value of a set point reflecting a desired value of the pressure differential effective to position the dispersion band.

An apparatus may be constructed to have a separator, separating a first liquid and a second liquid from each other. It may be characterized by an inlet receiving a mixture of the first and second liquids, and will establish a dispersion band therewithin between a bulk of the first liquid and a bulk of the second liquid. A first outlet discharges the first liquid, and a second outlet discharges the second liquid. Thus a cut (fraction) of the total flow that is represented by that liquid may be measured.

A control system positions the dispersion band automatically, based on the cut, the fraction of one of the first and second liquids in, and eventually separated out from, the mixture. The control system may include an inlet flow meter detecting a inlet flow rate of the mixture into the separator, a first or outlet flow meter detecting a flow rate of the first liquid through the first outlet, and a second or outlet flow meter detecting a second flow rate, that of the second liquid, through the second outlet.

The control system may be programmed to automatically adjust a pressure differential between the first outlet and the second outlet based on the cut. It may include a comparator automatically reporting a differential between the first and second pressures in order to control thereby a valve automatically positioning the dispersion band by controlling the differential between the two outlet pressures. The dispersion band location corresponds to equality between a first settling distance (e.g., average distance) corresponding to droplets of the second liquid migrating through the first liquid and a second settling distance corresponding to droplets of the first liquid migrating through the second liquid.

A corresponding method may include providing a separator, operating to separate first and second liquids from one another, and characterized by an inlet receiving a mixture of the first and second liquids, a dispersion band positioned between the first and second liquids, a first outlet discharging the first liquid, and a second outlet discharging the second liquid. Operation of a control system positions the dispersion band automatically based on the cut of either one of the first and second liquids.

By providing a processor controlling a pressure, the system separates the first and second liquids from one another in a separator. The system detects and provides to the processor, the cut. The positioning, by the processor, of the dispersion band is accomplished by changing the pressure differential between the first and second outlets according to a relationship with (e.g., equation relating it to) the value of the cut.

An inlet flow meter detects the inlet flow rate of the mixture, a first outlet flow meter detects a flow rate of the first liquid through the first outlet, while a second outlet flow meter detects a second flow rate of the second liquid through the second outlet. This information is processed to determine the cut. A processor programmed to automatically adjust a valve on the outlet corresponding to the lighter species or "phase" of liquid, can control the position of the dispersion band in the separator by controlling the pressure differential between the first and second outlet.

For example, sensing a first pressure at or near the first outlet and a second pressure at or near the second outlet, a processor, comparator, or both can compare a differential between the first and second pressures and position a control valve automatically to control that differential. The set point of that differential in pressure is determined by a relationship (e.g., equation) characterizing the position of the dispersion band to that differential. Thus, a processor automatically tracks the cut, the position of the dispersion band, and the backpressure, and adjusts the control valve to keep the dispersion band at its optimum location for the cut and material properties it detects in the system.

The dispersion band is held at a location corresponding to an equality between a first settling distance corresponding to droplets of the second liquid migrating radially through the first liquid and a second settling distance corresponding to droplets of the first liquid migrating radially through the second liquid. The settling distance is a product of a settling velocity and a residence time corresponding to the properties of the separator, the first liquid, and the second liquid at operating conditions.

For example, the first liquid corresponds to a first residence time reflecting a first bulk flow thereof from the inlet to the first outlet. The second liquid corresponds to a second residence time reflecting a second bulk flow thereof from the inlet to the second outlet. Automatically positioning the dispersion band to equate settling distances of the liquids may be based on an average settling velocity and an average residence time for each. The calculations will depend on current fluid properties and the operational characteristics of the separator, such as geometry, angular velocity, and so forth.

A tank, e.g., such as a fracking fluid tank re-purposed to hold oil, may be rolled (pumped between distant corners, from near the bottom to near the top). The contents is "slop oil" (not meeting specification), is "effectively inseparable," not separable by gravity in a commercially reasonable time (a day to three; a week usually being per se unreasonable). Some is inseparable indefinitely.

In certain embodiments of an apparatus and method in accordance with the invention, such a tank full of off-spec. oil or material to be separated may be received into the tank, have additives introduced into the tank as its contained contents, be closed up or locked, and then circulated, commonly referred to as "rolling." Thereafter, the tank will be permitted, or its contents will be permitted, to rest. Resting may occupy a day or more. Resting is particularly directed to permitting some degree of settling out by contaminants. Contaminants are typically referred to as basic sediments and water (BS&W).

In a system and method in accordance with the invention, the contents of the tank may be tested by extracting a sample (thief test) from an upper port accessing the very highest contents in the tank. Thereafter, calibration may occur of a water meter or BS&W meter. In one embodiment, a BS&W meter may simply be a capacitance measuring device directed to measuring capacitance within the fluid. Capacitance has a regular relationship or predictable relationship with water content.

Nevertheless, certain production oil may have more or less water, and may have other properties that effect capacitance. Therefore, each batch of oil should be sampled, and the BS&W meter calibrated in order that the actual BS&W content may be tested, online, directly from the flow as the tank is emptied.

Following calibration of a BS&W meter, dehydration may begin by snorkeling or otherwise emptying or drawing out content from the tank, beginning at the top. The content will then be passed through a liquid-liquid separator. One suitable separator is a centrifuge in accordance with the invention as described hereinabove.

Ongoing testing continues to test the oil output from the centrifuge by the BS&W meter that is sampling the output to a sales tank. If the oil remains within the BS&W specification required, then draining or emptying the source tank, best done by snorkeling, continues.

To the extent that the separator cannot maintain quality, then any straying of the BS&W content out of specification results in another test that determines whether the influent flow from the line can be reduced. That is, can the dwell time be increased in the separator? So long as the dwell time can be increased, then the flow rate into the influent line will be reduced. This may be done by changing valve settings, changing pump outputs, or the like. So long as the flow of influent into the line may be adjusted, that adjustment will take place and the snorkeling or withdrawing of content will continue.

Ultimately, a pump or valve will reach its limit of performance and can no longer reduce the flow of influent to the centrifuge. At that point, snorkeling or other withdrawal from the source tank must cease. No more content (typically oil) can be withdrawn and still be processed to stay within its market specification.

It can be seen that this mechanism of controlling, testing, and always drawing from the top of the content of a tank results in all oil in a sales tank being within specification. Thus, the entire load will always be within specification.

In certain embodiments, the bottoms or sludge in an undisturbed region near the floor of a tank will accumulate during continuing operations. Accordingly, once withdrawal has stopped, the depth of the bottoms or sludge may be tested to determine whether the accumulation is less than the maximum permissible. For example, outlets from a tank may be spaced some distance above the floor so that entrainment of the sludge at the bottom thereof will not occur. Allowing too great a build up of the sledge on the floor will eventually interfere with the pumps and lines used to roll or churn the contents of the source tank.

Thus, if the depth of the tank bottoms or sludge is sufficiently low, has not reached a maximum allowable, then draining content may continue. In fact, the source tank may be refilled and processed through the entire scheme of receiving, introducing additives, locking, rolling, resting, calibrating, and withdrawing or snorkeling content out. Alternatively, a source tank may be repurposed to some other need once emptied. Ultimately, once the depth of the bottoms rises above the maximum permissible, then the source tank must be purged of that sludge.

Operation of a tank, such as a tank trailer, a snorkel drain, an annular snorkel drain that can readily drain both desirable content and residual sludge, as well as the separation centrifuge may all be understood by reference to the documents incorporated hereinabove by reference.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 6 is a chart illustrating the Stokes Law equation as applied to a liquid droplet moving or drifting within a separator in accordance with the invention;

FIG. 7 is an equation describing the concept of a settling length (distance) in accordance with the invention;

FIG. 8 is a chart defining an equation relating the dispersion band radius to the heavy cut (heavy phase fraction in a flow) for a separator, and accordingly the relationship governing the set point for a dispersion band radius set point in accordance with the invention;

FIG. 9A is a chart providing an equation relating the water volume fraction to the dispersion band radius for a specific geometry of an embodiment of a rotating separator in accordance with the invention;

FIG. 9B is a chart providing a description of an equation relating the water volume fraction as a function of dispersion band radius, for a different geometry, the equation of FIG. 9A applying to cylindrical geometries, and the equation of 9B applying to conical geometries, both of which exist in different locations in one embodiment of an apparatus in accordance with the invention;

FIG. 10 is a chart providing an equation defining the pressure differential existing between the output line of a lighter phase effluent compared to the pressure in the heavier phase effluent line, as a function of the dispersion band radius, the geometry of the separator, and the rotational velocity in radians per second of the rotating separator;

DETAILED DESCRIPTION OF THE PREFERRED EMBODIMENTS

Figure 1:
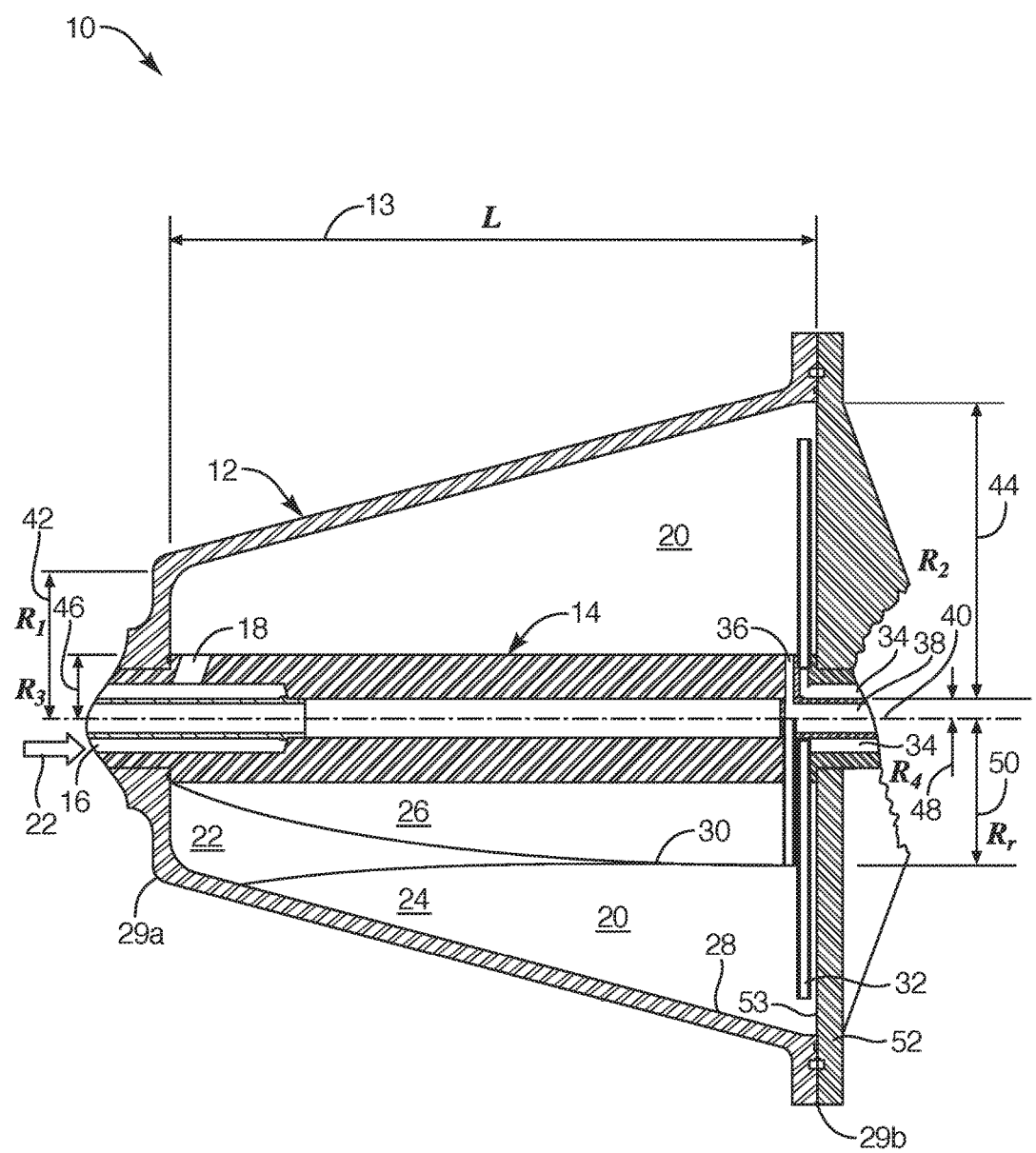
FIG. 1 is a side, elevation cross-sectional view of one embodiment of a rotating separator in accordance with the invention, illustrating a dispersion band or interface between two liquid phases distinct from one another and being separated from an incoming mixture.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Referring to FIG. 1, a system 10 may be embodied as a separator, and may specifically be embodied as a rotating separator. In the illustrated embodiment, the system 10 involves a shell 12 that is circular in cross section, perpendicular to an axial direction, and is trapezoidal with respect to a transverse or radial axis perpendicular to the center line 40.

In the illustrated embodiment, the shell 12 may be a forged, or fabricated shell built to be supported on and rotating with a central shaft 14 or simply a shaft 14. The shaft 14 is hollow, and traverses the entire length of trapezoidal shape of the shell 12 to define an interior length 13 or length 13 of operation. Meanwhile, the shell 12 contains a liquid that originates with a line 16 containing an influent. The line 16 is represented as a annulus embedded within the shaft 14, eventually opening up through an access 18 or port 18 to expose the chamber 20. Thus, an influent material 15 passing through the annulus 16 exits out the access 18 or port 18 into the chamber 20 for separation.

Typically, the influent 22 is a mixture of a heavier phase 24 or heavier species 24, and a lighter phase 26 or lighter species 26. The two species 24, 26 or phases 24, 26 combined as a mixture 22 in the influent 22 are contained by the wall 28 or inner surface 28 of the shell 12. Likewise, they are bounded at the inside radius by the shaft 14. Accordingly, the species 24, 26 separate from one another as they traverse from one end 29a of the shell 12 toward the opposite end 29b of the shell 12.

They separate to and across opposite sides of an interface 30 or boundary 30. This interface 30 or boundary 30 actually represents a dispersion band 30 of finite thickness, constituting the last vestiges of the mixture 22. Along the length 13 of the chamber 20, the bulk flow is from the inlet end 29a toward the outlet end 29b, for the bulk of both phases 24, 26.

Meanwhile, and simultaneously with that bulk flow, individual droplets of each species 24, 26 are migrating (each within the opposite species 26, 24, respectively) toward that dispersion band 30. Thus, to a certain extent, the dispersion band 30 represents the boundary of coalescence of each droplet as it passes out of its foreign species 26, 24, and back into its own species 24, 26, respectively.

Ultimately, as described in U.S. patent application Ser. No. 61/814,760, incorporated hereinabove by reference, the comparatively heavier species 24 eventually exits the chamber 20 through the standpipe 32 or pickup tube 32. The pickup tube 32 drains the heavier species 24 or heavier phase 24 from the chamber 20 and into the annulus 34 at the exit end 29b of the system 10. Meanwhile, the separated and comparatively purified lighter species 26 or lighter phase 26 is drained out through the port 36 in the shaft 14 to exit the system 10 through the conduit 38 along the center line 40 of the shaft 14.

The geometry of the system 10 is defined by several characteristics or parameters. For example, a radius 42 represents the inside radius or minimum radius of a trapezoid of revolution. That is, in this embodiment, the shell 12 represents a frustum of a cone. Accordingly, the radius 42 defines the minimum diameter of that cone. Similarly, at the opposite end 29b of the shell 12, the maximum diameter of the trapezoid of revolution is defined by the radius 44.

The radius 46 represents the outer radius 46 defining the outer diameter of the shaft 14. This is the radius at which the port 36 will typically draw off the comparatively lighter species 26 to be discharged through the conduit 38.

The radius 48 represents the radius 48 of the innermost surface of the annulus 34 fed by the pickup tube 32. The significance of the radius 42 is that it constitutes the maximum radius at which the flow in the chamber 20 may be considered to define a cylindrical envelope of the length 13. Meanwhile, the distance between the radius 42 and the radius 44 represents that portion of the chamber 20 inside the shell 12 that is effectively a volume of revolution of a triangle.

A significance of the radius 46 is that it represents the minimum radius 46 at which the dispersion band 30 could be positioned. Even so, this is a theoretical value inasmuch as the dispersion band 30 cannot be allowed to disappear and the system 10 still operate. Similarly, the significance of the radius 48 is that it represents the floor or the lowest or smallest radius 48 at which the heavy column, or the column constituted in the heavier species 24, may be considered to rest in measuring the value of head.

The radius 50, also called $R_i$ 50, represents the radius at which the dispersion band 30 or the interface 30 between the heavier phase 24 (heavier species 24) and the lighter phase 26 (lighter species 26) come together. As a practical reality, the dispersion band 30 actually begins as the mixture 22 between the phases 24, 26. It 30 eventually narrows as the respective droplets migrate out of their opposite phases 26,24 from the mixture 22, and coalesce or agglomerate with the bulk of their own phases 24, 26, respectively. Toward the cap 52 or lid 52 that seals the chamber 20 of the rotor 12 or shell 12, the interface 30 or dispersion band 30 degenerates to almost a mere surface across which the final transfer of droplets occurs as the two phases 24, 26 fully separate to the degree specified for the operation of the system 10.

The interface 30 stagnates at the surface 53 of the lid 52. Rather, the boundary simply exists along that surface 53 or wall 53. The bulk flow in each of the respective phases 24, 26 will all exit the chamber 20 through the pickup tube 32 and the port 36, respectively.

Figure 2:
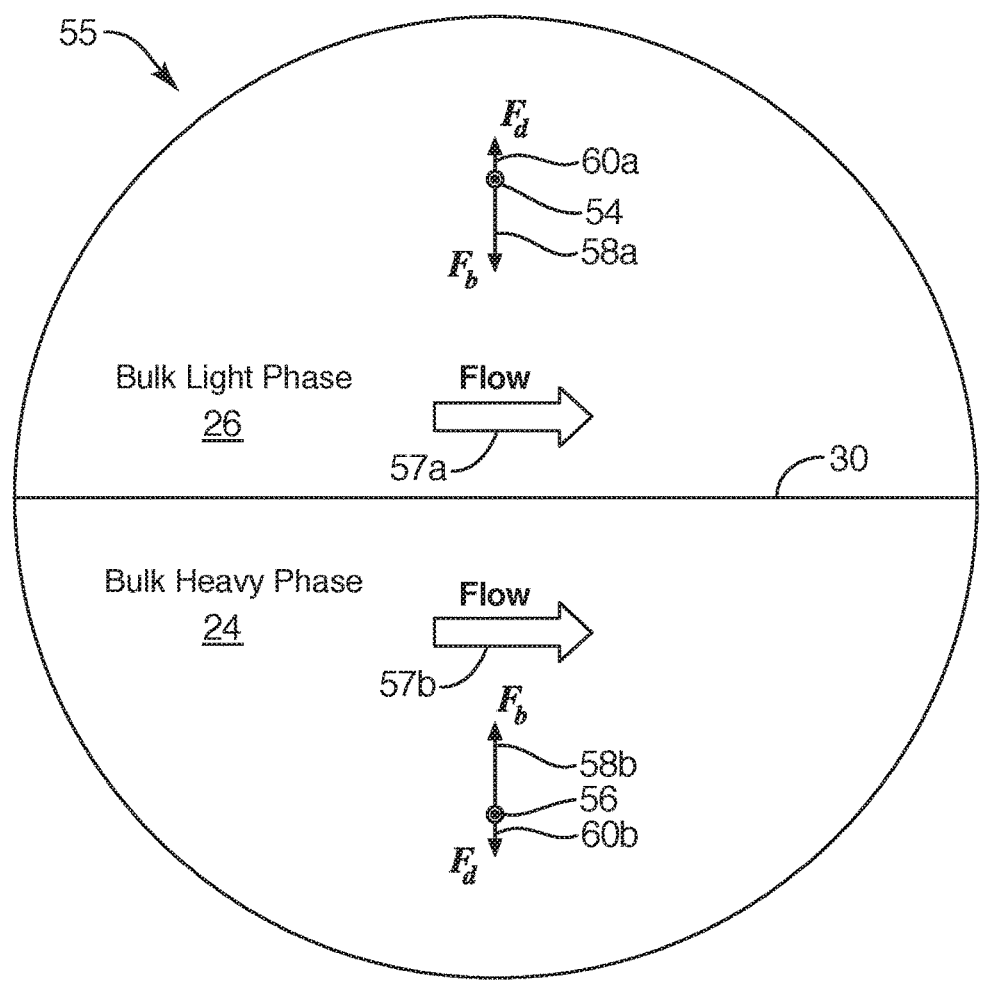
FIG. 2 is an expanded schematic, side elevation view of the dynamic relationship between droplets of heavy and light species (phases) migrating out of light and heavy species, respectively, toward a phase interface or dispersion band of a separator such as the separator of FIG. 1.

Referring to FIG. 2, a region 55 of the cavity 20 about the dispersion band 30 is illustrated. The bulk flow 57a of the light phase 26 is traveling in the same direction as the bulk flow 57b of the heavy phase 24. Within the bulk flows 57 (the trailing letter represents a specific instance of the item identified by the leading reference numeral) the droplets 54, 56 are migrating toward the dispersion band 30 or interface 30.

At the same time, they are entrained with and travel with the bulk flow 57. In the illustration, a droplet 54 represents a droplet 54 of the heavy phase 24 captured within or surrounded by the bulk light phase 26. Accordingly, a density differential between the density of the droplet 54 and the surrounding bulk light phase 26 results in a buoyant force 58a acting on the droplet 54 to urge it or drive it toward the dispersion band 30.

Meanwhile, a drag force 60a is identified by the symbol of $F_d$. The drag force 60a is governed by the same set of drag equations known in the art of fluid dynamics. That is, with motion, any object (e.g., droplets 54) within a fluid environment, such as the bulk light phase environment 26, experiences fluid drag related to the properties of the fluid environment 26, the size and shape of the object 54 (in this case a droplet 54) and the square of the relative velocity of the object 54 to the environment 26.

Therefore, the buoyant force 58a identified by the symbol $F_b$ 58a acting to move the droplet 54 composed of the heavy phase 24 toward the dispersion band 30 is resisted by the drag force 60a identified by the symbol $F_d$ 60a that is directly related to the geometry, velocity squared, and so forth as above. Thus, the droplet 54 will come to some terminal velocity at which it will then drift toward the dispersion band 30. Meanwhile, the bulk flow 57a of the light phase 26 also carries the droplet 54 downstream from a location proximate the inlet end 29a of the rotor shell 12 toward the terminal end 29b thereof near the lid 52.

A droplet 56 comprising a small portion 56 of the light phase 26 is surrounded entirely by the bulk heavy phase 24 in a flow 57b moving from the inlet end 29a toward the outlet end 29b of the rotor shell 12, or cavity 20. Again, a buoyant force 58b acts on the droplet 56 in accordance with the density difference between the two species 24, 26 or phases 24, 26. Similarly, based on the velocity, the geometry, and the fluid properties, the drag force $F_d$ 60b also operates to impose a terminal velocity on the droplet 56 in the direction toward the interface 30 or dispersion band 30.

Figure 3:
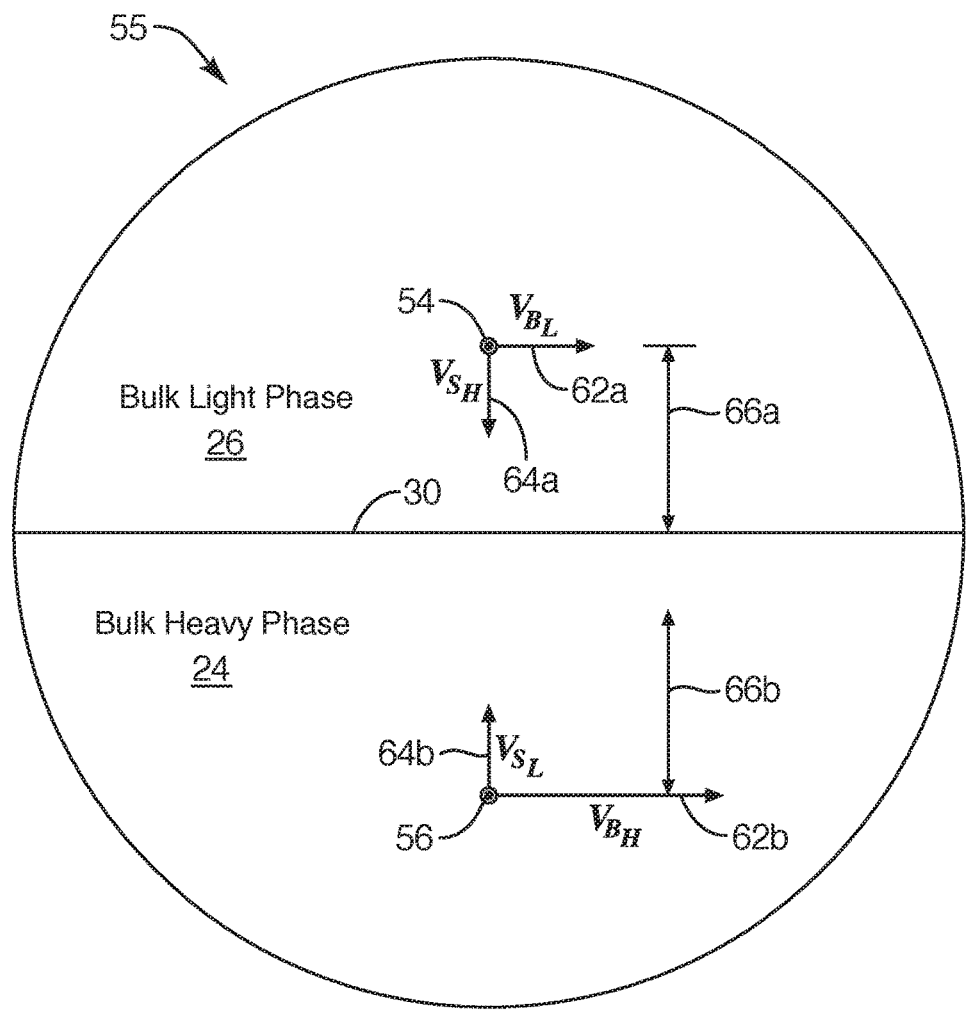
FIG. 3 is a schematic diagram of the phenomena operating on the droplets of FIG. 2, in this case illustrating the relationships between droplets having differential densities, in bulk phases having disparate viscosities and densities, thereby establishing two components of velocity of droplets in a separator, and particularly the parameter of settling distance or length to be matched between species (phases) in a separator in accordance with the invention.

Referring to FIG. 3, the droplets 54, 56 are shown, each with the contributing velocity vectors 62, 64 contributing to their net velocities. Given the bulk flows 57a, 57b having basic velocities 62a, 62b, each droplet 54, 56 will have a velocity component 62 tending to be directed from the inlet end 29a toward the outlet end 29b of the cavity 20. The net force balance will result in a net positive force on each droplet 54, 56 toward the dispersion band 30. That force balance results in a velocity vector 64 corresponding to each of the droplets 54, 56. For example, the heavier droplet 54 in the bulk lighter phase 26 will have a component vector 64a of velocity at which it travels toward the dispersion band 30. Similarly, the comparatively lighter droplet 56 will have a component velocity vector 64b driving it toward the dispersion band 30.

This definition of the migration velocity 64 or settling velocity 64 applicable to any droplet moving in a liquid-liquid separator 10 allows us to define a mathematical relationship. That mathematical relationship actually represents a physical condition or can be used to define a physical condition. A velocity of a car along a road represents an amount of distance covered in an amount of time. That characteristic velocity is often referred to miles per hour or kilometers per hour. It may be measured in furlongs per fortnight, but the more common expressions are well understood as feet per second, meters per second, miles per hour, or the like. It is a distance covered over some period or measurement of time.

Integrating a velocity through a period of time results in defining a distance. A car traveling at a velocity for some period of time will traverse a certain distance. Thus, in an apparatus and method in accordance with the invention, a settling distance 66 may be defined for any droplet 54, 56 in a liquid-liquid buoyancy condition of a separator 10. The droplet 54 may have a settling velocity 64a that will operate over some period of time, such as the dwell time that the droplet actually is traversing along the length 13 of the cavity 20. Some droplets 54 will be closer to the dispersion band 30 at the inlet end 29a, and thus will spend comparatively little time making their way toward the dispersion band 30. Others will be located at the wall 28 of the shell 12, and thus will take a maximum time to drift to the dispersion band 30.

Therefore, in a system and method in accordance with the invention, Applicants define a settling distance 66 to be the product of a settling velocity 64 and a residence time of a droplet 54, 56 within the chamber 20 of the system 10. As a reality of flow dynamics, very few of the droplets actually perform according to any average. Some will have a maximum distance travelled, some will have a maximum velocity, but one may define an average. Thus, a residence time or dwell time of any chamber 20 may be defined as the bulk volumetric flow rate divided into the total volume of the chamber 20. Accordingly, one may think of one dwell cycle or one residence period or residence time as the time to completely flush the chamber 20 on average. Thus, one may define a bulk velocity 62 in terms of that residence time. In fact, once a system is operational and the cut (fraction) of one species relative to the total inflow 22 can be defined, one may actually define a bulk velocity 62a for the lighter phase 26, and a different bulk velocity 62b for the heavier phase 24.

Likewise, one may define the average settling velocity 64a for a heavier droplet 54 in the lighter phase 26, and an average settling velocity 64b of a lighter droplet 56 within the heavy phase 24. Of course, each of those settling velocities 64 will depend upon the droplet 54, 56, its average size, its density difference with its surrounding environment, the viscosity of the surrounding fluid 24, 26, and so forth. However, on average, such properties may be calculated, as may the geometries. Meanwhile, the times may be established by certain input parameters and operational characteristics of the system 10. Thus, Applicants define an average settling velocity 64 for each type of droplet 54, 56, and a settling distance 66a, 66b, respectively, corresponding thereto.

Applicants have investigated various geometries, material properties, performance parameters, and construction mechanisms, and so forth in liquid-liquid separators. These systems have not appeared to operate according to conventional settling theory, nor to yield to the calculations and rules of thumb that have been central to settling system design and theory over decades.

For example, conventional settling theory in a gravitational system in which a tank is stationary does not have a change in the available settling area or the surface area of the dispersion band 30 in the tank. This is understandable inasmuch as the tank is stationary, and at a steady state operational condition. The dispersion band 30 should stabilize at a particular location, but its area is incapable of changing.

Since conventional settling theory teaches that one should maximize the settling area of then such a system has no change in area, and has no theoretical change in performance regardless of inlet conditions.

As a practical reality, those skilled in the art have observed that performance does change with the fluid mixture, the fluid properties, and the cut (fraction of one separated species compared to the net bulk mixture input). Thus, settling theory as existed in the prior art must acknowledge that it does not resolve or address all the phenomena occurring in the settling process.

In dealing with rotating settlers, or settling systems with either rotating vanes within a stationary cylindrical tank or a rotating cylindrical tank or other shape, settling theory suggests that the maximum available area should be used for positioning the dispersion band 30 in the settler.

In the trapezoidal shape of the system 10, Applicants applied settling theory to determine that the maximum area should be the controlling parameter for optimizing or otherwise insuring optimum performance of the system 10. Accordingly, calculations were made of the geometries, and a radius 50 was established that provided the maximum available area (the surface of revolution defined by the dispersion band 30) for the system 10.

One will note that the trapezoidal shape decreases the area by decreasing the net fraction of the total length 13 of the shell 12 occupied by the dispersion band 30 as the radius 50 is increased. That is, the dispersion band 30 moves along the wall 28, becoming shorter as the radius 50 increases.

The area of a cylinder represented by the dispersion band 30 as a cylinder of revolution 30, increases in area as a function of an increase in radius 50. Thus, the reduction of the length of the dispersion band 30 operates counter to the increase in the circumference of the dispersion band 30 with an increase in radius. Thus, there is a maximum value of area that can be found for the trapezoidal geometry of the system 10.

Applicants applied settling theory to the set up of the system 10, operating the radius 50 at the position or value that provides a maximization of the net surface area of the dispersion band 30. The results, while not unreasonable, did not provide experimental data suggesting that settling was optimized or that settling rates, purity of separated species 24, 26, or the like were optimized.

One may then consider the effectiveness of the average residence time or settling time, the phenomena actually occurring within the system 10 that drive the settling rates, the eventual purity of the separated species 24, 26, or other parameters. Particularly, which input parameters of fluids, quantities, velocities, operational speeds, fluid characterizations, geometries of the system, and so forth may contribute to or control any parameter output by the system 10 or characterizing an output of the system 10?

Figure 4:
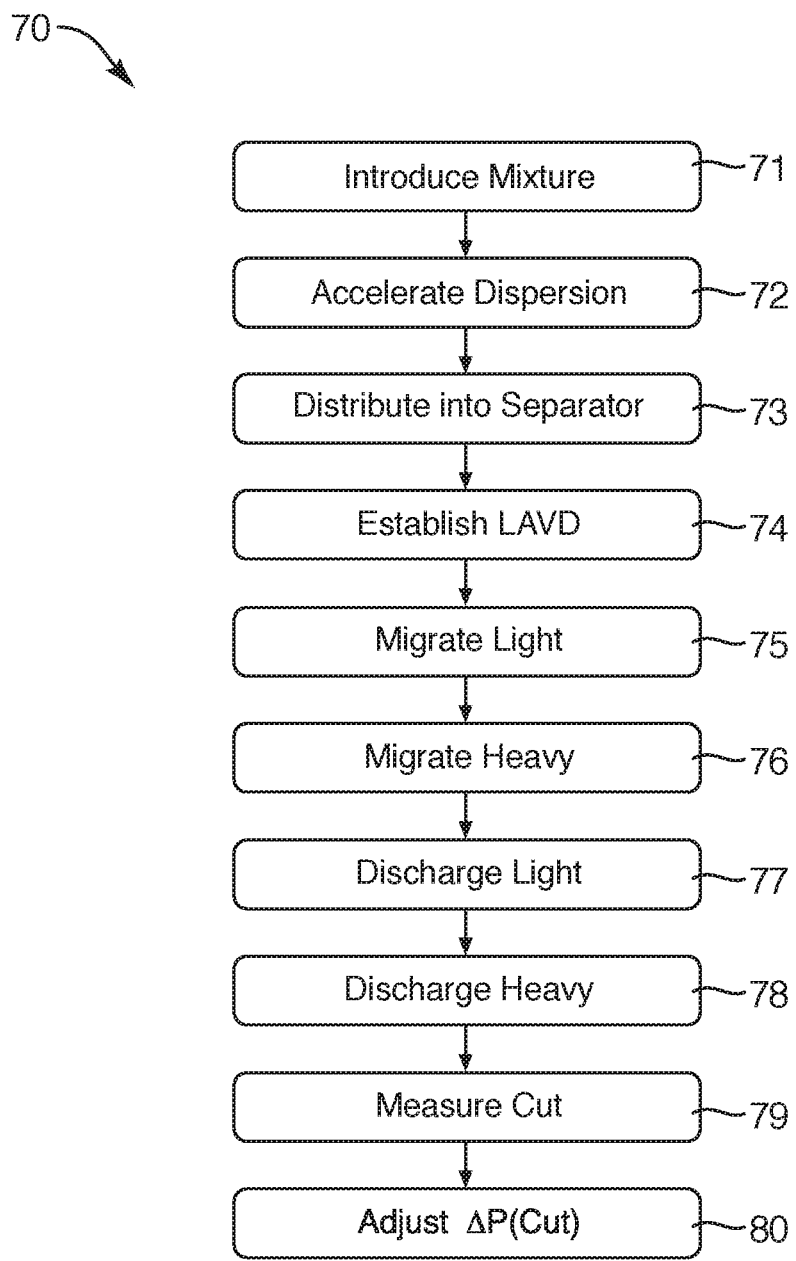
FIG. 4 is a schematic block diagram of a process for separation of species for phases in a liquid-liquid separator in accordance with the invention.

Referring to FIG. 4, a process 70 represents a method 70 for separation using a system having a geometry consistent with the invention. For example, for a geometry characterized in FIG. 1, the process 70 may begin with introducing 71 a mixture 22 into the influent annulus 16 of the system 10. Immediately, as the flow is exposed to the rotating of the shell 12 and its associated fixtures, accelerating 72 the dispersion 22 or mixture 22 will occur within the shaft 14. However, as described in the documentation incorporated hereinabove by reference, the access 18 or port 18 actually constitutes a series of ports 19 shaped specifically to accelerate 72 the dispersion 22 in the rotational or circumferential direction.

Those mechanisms will also then distribute 73 the influent 22 across the entire volume and diameter at the inlet end or near the inlet end 29a of the shell 12. Likewise, through the hardware systems described in the reference materials incorporated by reference, and not illustrated in FIG. 1, establishing 74 a laminar, annular, velocity distribution (LAVD) will occur comparatively quickly compared to prior art systems near the inlet end 29a.

Migrating 75 by the lighter phase 26 and migrating 76 by the heavier phase 24 will then occur naturally, driven by the pumping that is driving the influent 22 into the shell 12. As the migrations 75,76 progress through the cavity 20 of the shell 12, the respective flows 57a, 57b of the light phase 26 and the heavy phase 24, respectively, will continue during a migration 75 of the light species 26 toward the bulk light phase 26.

Migrating 75 by the light phase 26 may be thought of as two migrations, including both migrational flow 57a toward the terminal end 29b of the shell 12, as well as a migration of the lighter droplets 56 toward the bulk light phase 26 through the dispersion band 30. By the same token, migrating 76 by the heavy species 24 constitutes both the bulk migration of the flow 57b from near the inlet end 29a toward the outlet end 29b, but also the movement of the heavier droplets 54.

For example, the heavier droplets 54 will tend to migrate as a result of buoyant forces 58a toward the bulk heavy phase 24 by way of passage through the dispersion band 30. Of most interest, is the migration 75, 76 of the respective light phase 26 and heavy phase 24 toward the dispersion band 30 in order to effect purification separation of each from the other.

Ultimately, discharging 77 the separated light phase 26 and discharging 78 the separated heavy phase 24 will occur through the port 36 and pickup tube 32, respectively. Likewise, these outlets 36, 32, will also discharge their flows into the core conduit 38 and the shaft annulus 34, respectively.

At this point, one may measure 79 the cut. Since flow meters may disclose the total volumetric flow rate or mass flow rate of the mixture 22 or influent 22, a measurement of either one or both of the light phase 26 and heavy phase 24 being discharged 77, 78 will allow a simple arithmetic calculation 79 of the cut or fraction that either species 24, 26 constitutes of the total incoming influent 22.

In the separation process, one may then adjust the pressure differential existing between the lightweight carrier conduit 38 and the heavy species carrier 34. Adjusting 80 that differential will typically take the character of a pressure back up or a pressure rise within the lighter phase 26 (the central conduit 38). That differential in pressure phenomenologically will back up the oil flow 57*a* or lighter phase flow 57*a* causing a larger fraction of that species 26 to exist within the cavity 20 of the shell 12. Therefore, the dispersion band 30 will necessarily move outward, increasing the radius 50 at which the dispersion band 30 persists.

With this mechanism set up in a system 10 in accordance with the invention, the separation process 70 was at least controllable to move the dispersion band 30 or alter the radius 50 at which the dispersion band 30 exists and persists. Thus, Applicants were able to manipulate the position of the dispersion band 30 at will. Also, it was possible to measure 79 the cut of either species 24, 26. Moreover, it was now possible to alter influent conditions, temperatures, or other parameters and test the quality of the effluents discharged 77, 78.

Applicants were now prepared to conduct experiments on what parameters will affect the properties of an effluent discharged 77, 78, system 10 in accordance with the invention. Likewise, Applicants were in a position to manipulate the position of the dispersion band 30 in order to determine the effect of dispersion band position on any particular qualitative or quantitative characterization of input parameter, the effluents discharged 77, 78, or both.

Figure 5:
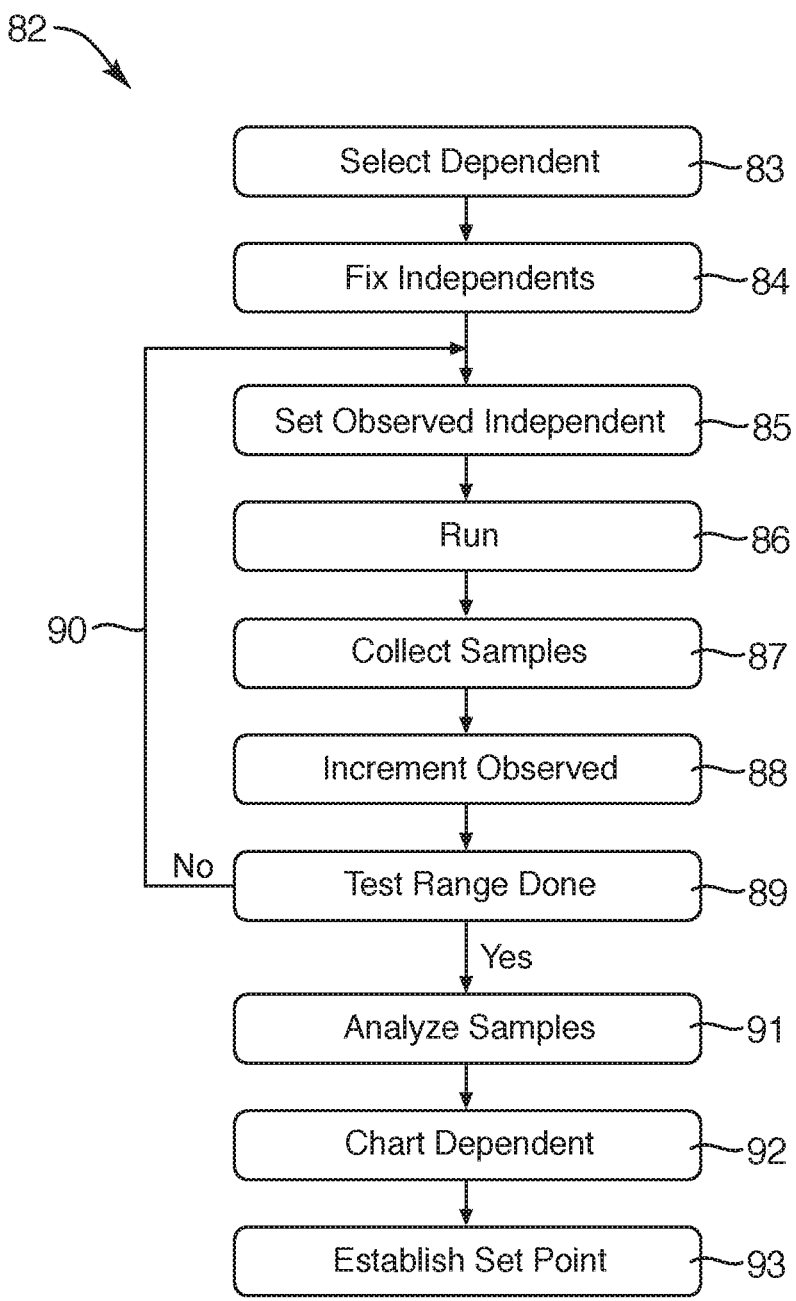
FIG. 5 is a schematic block diagram of an experimental procedure for establishing the set point for optimizing the separator performance by establishing the optimum position of a dispersion band at the optimum radius in a separator in accordance with the invention.

Referring to FIG. 5, a method 82 for investigating optimization may be conducted, such as determining values of parameters for optimization of design or operation, or determining whether optimization is possible. In an experiment in accordance with the invention, Applicants developed a process 82 for conducting the experiment. Initially, selecting 83 a set of dependent variables involved in identifying various dependent variables that were to be considered. For example, one may question what an operator of a system 10 in accordance with the invention desires to optimize. The outputs or optimized parameters are dependent variables that one desires to set at an optimum value. A purity of an effluent 24, 26 may be important. Reducing the amount of water 24 in a flow of oil 26 improves the value of the oil. Likewise, extracting all of the oil 26 possible out of an influent 22 also saves or commits to commerce an amount of oil that might otherwise be wasted.

In production from oil wells, any water discharged into a discharge well or reinjection well not only costs the loss of that oil to the production of a well, but also tends to foul the injection well and reduce its lifetime. Improving water quality in order to minimize the amount of entrained oil 26 in a flow of separated water 24 improves injection well performance and longevity, improves the value of the water 24, and may otherwise render the water more useful. Increasing the purity of oil 26 extracted from water 24 may be a parameter to be optimized, on the other side of the process.

Thus, the condition of the effluents 24, 26 or either one of them may be an important parameter. Not only may some criterion to be met be significant, but not exceeding that criterion may also be an important consideration. For example, once oil has a water fraction of less than one percent in a crude supply, a refinery typically offers no additional premium. Thus, meeting the one percent criterion is economically important. Exceeding it is of no particular value. Thus, optimization at just under the one percent criterion is a maximum commercial benefit, at a minimum processing cost to meet that criterion.

Similarly, waters may be similarly situated for environmental issues. The parts per million or parts per billion permitted for hydrocarbons in a water flow passed into an estuary or marine environment may be as low as five parts per million. In contrast, if a flow of a water stream 24 is going to be discharged into a sewage treatment plant for additional processing, the permissible level of contamination may be as high as about one hundred parts per million. Thus, depending on the ultimate destination, a flow of the heavy phase 24 (e.g., water) may be optimized to meet the required criterion, but not exceed it by a value that would increase the cost of processing to no economic avail.

Other dependent variables may be selected 83. All need not and may not necessarily be selected, but selection may include several parameters. One may typically select 83 at least one parameter to be optimized, and other parameters may follow it. However, certain performance parameters may actually move in an opposite direction when one parameter is optimized.

Thus, for example, some parameters that may be optimized may include maximum throughput of the influent 22, maximum output of any one of the effluents 24, 26, minimum concentration of a particular contaminant in a particular one of the effluents 24, 26, minimum energy requirements to process the influents 22, such as pumping power, rotational power, and so forth, or the like. Also, for economic efficiencies, it may be valuable to minimize the down time of operation of the system 10 within some other criterion. For example, one may wish to meet some criterion for output quality, but do so at a minimum power, or minimum cleaning cost, minimum down time, or the like.

Upon selecting 83 a dependent variable, one may then fix 84, by selecting and setting, independent variables that contribute to the operation of the system 10. For example, temperature of the influent 22 is a parameter that must be dealt with. A flow from a production facility, or a collection facility may simply have whatever the temperature is for the environment, the influent 22, and the like. A hot Arizona sun or a cold Montana winter may dictate the temperature. A heater may adjust it.

The effect of temperature may be investigated by fixing 84 temperature as one of the independent variables that will affect the overall performance of the system 10.

Meanwhile, the mass flow rate of the influent 22, the input cut of an influent 22, and the like may affect performance. Between sources, such as wells, between days, or between seasons, a production facility may see various mass flow or volumetric flow rates, and different fractions or percentages of the heavy species 24, light species 26, and other contaminants. Thus, it was useful to experiment in the procedure 82 with the effect of such independent variables that may dictate performance later, and must be accommodated by whatever operational parameters may be adjusted in the system 10.

Ultimately, the geometry of the system 10 may be comparatively fixed with respect to any one design, but those parameters should be tracked and fixed 84 as independent variables. Meanwhile, certain other variables, such as the rotational frequency or the speed of rotation of the shell 12 may also be set. The point of fixing 84 the independent variables is actually not to fix them but to be able to set them at a value while variations in other parameters are tested. Independent variables may be re-fixed 84 at different values in order to see what the sensitivity of operation of the system 10 is to those particular variables.

One benefit provided by the process 82 is the ability to deal with independent variables fixed 84 by incoming conditions that cannot be readily changed in operation. Determining what operational parameters can be used to manipulate the results from a system that has a set of fixed 84 independent variables may perhaps accommodate such conditions.

As a practical matter, the fixed 84 independent variables will typically be those that are difficult to alter in operation. In contrast, the experiments 82 are designed to test other parameters that may be more readily manipulated in order to determine the sensitivity of operational system 10 to those additional observed variables.

Accordingly, the setting 85 of observed independent variables may next be done. These may be variables such as the backpressure differential between the output lines 34, 38. Similarly, an observed variable may be the radius 50 at which a dispersion band 30 exists.

Upon setting 85 an observed independent variable to be tested, one may then run 86 or operate 86 the system, taking data on mass flow rates, pressures, and other parameters of interest. Collecting 87 various samples may permit establishment of the condition or quality of each of the effluent bulk flows 57a, 57b of the light phase 26 and heavy phase 24 being separated. Collecting 87 samples may be particularly important for tests that cannot necessarily be done online, but may require slower or offline laboratory procedures later. Collecting 87 may involve collecting streams, diverting streams, or collecting fixed volumes of samples, with all their corresponding data characterizing the operational conditions, influent 22 conditions, and so forth.

Incrementing 88 the observed independent variable may then be conducted throughout a range. For example, a total range from minimum value to maximum value may be set. Accordingly, following incrementing 88 from some start value, testing 89 will determine if the range has been completely covered. For example, typically a range may include some contemplated range of values between extremes expected in operation.

Typically, an increment value for an incrementation 88 will be from about one percent to about ten percent of the overall range. Thus, following incrementing 88, a test 89 determines whether testing over the range has been completed. If not, then the return 90 sets 85 the observed independent variable. Collecting 87 is repeated, followed by more incrementing 88.

Eventually, the test 89 reports or records that the range has been completed. Thus, an affirmative answer to the question of whether the range has been completed results in analyzing 91 and charting 92 (e.g., curve fitting 92) the dependent variable or variables selected 83 in the process 82, for analysis. Accordingly, establishing 93 a minimum or maximum value may effectively determine an establishment 93 of a set point at which the observed independent variable may be set to obtain the optimization of the selected dependent variable 83 that results.

Referring to FIGS. 6 through 10, a system of equations is presented to define certain phenomena, and to characterize the process of experimentation and optimization resulting from the investigations of Applicants. For example, FIG. 6 represents a form of Stokes' Law establishing a velocity. This velocity corresponds to the settling velocities 64 identified in FIG. 3. FIG. 7 presents a definition of a settling length corresponding to the settling distance 66 identified in FIG. 3. FIG. 8 presents a ratio for cut, this one identifying the cut or fraction of the heavy species 24 or heavy phase 24 compared to the total flow of influent 22. That cut or fraction bears a relationship to the radius 50 at which the dispersion band 30 is set.

FIG. 8 results directly from applying the principle postulated or proposed by Applicants in FIG. 3. The experimental process 82, and data described hereinbelow, demonstrated the limitations on (inability to) classical or conventional settling theory to define, explain, or optimize performance of a system 10 in accordance with the invention. The principle of equating the settling distances 66a, 66b to each other in the system 10 of FIG. 3 results in the equation 3 of FIG. 8.

FIGS. 9A and 9B are definitions of the water (heavier species 24) volumetric fraction as a function of the radius 50 or $r_i$ in the equation, and represented by the $R_i$ 50 as the set point in FIG. 1. FIG. 9B defines the same water volume fraction or the cut of the heavier species also as a function of the radius $R_i$ 50 at which the dispersion band 30 is set.

However, the equation 4a of FIG. 9A applies whenever the dispersion band 30 is at a radius $R_i$ 50 less than or equal to the radius 42 called $R_1$ in FIG. 1. Meanwhile, outside that cylindrical volume or that volume of revolution is the angled wall 28 of the shell 12 for which equation 4b of FIG. 9B applies.

When the radius 50 is greater than the radius 42 called $R_1$, then the equation 4b of FIG. 9B applies. These equations, however, are specific to a specific geometry for the experiment and the device 10 of that experiment done in accordance with the procedure 82. Different geometries will require retreat to the original equations, and development of those geometric relationships to provide equations analogous to the equation 4a and equation 4b, but particular to the geometries of those systems.

However, the fluid properties are already accommodated by the equation 3 of FIG. 8. Similarly, the settling length l (El, a lower case L)$_s$ defined in equation 2 of FIG. 7 also applies regardless of geometry, fluid properties, or the like.

Applicants, based on the experiment 82 in a system 10 in accordance with the invention, proposed a theory of control and optimization of separators 10 by matching the settlement distances 66a, 66b of the principal species 26, 24, respectively separating across a dispersion band 30 in a system 10. To that end, to match the settling distances 66a, 66b in a system 10, one must solve several equations simultaneously for the values of unknown variables. Those equations are equation 3 from FIG. 8 and equation 4a from FIG. 9A within the region of the cavity 20 of the shell 12 within the radius 42, or with the equation 4b of FIG. 9B within the region outside the radius 42 in the cavity 20 of the shell 12.

Out of that simultaneous solution of equations comes a value of the radius 50. This is the value at which a dispersion band 30 should be set to equalize the settling distances 66a, 66b in the cavity 20.

The actual location within the shell 12 of the dispersion band 30 cannot normally be detected directly. At the centripetal forces imposed on a rapidly rotating structure 10 in accordance with the invention, sight glasses are not appropriate. Rather the radial height of each column of fluid (light 26 and heavy 24) may be detected by measuring the pressure (a reflection of the head or the head height) of each column of the heavy 24 or light phase 26 in the cavity 20.

For example, from the dispersion band 30 to the conduit 38 as a baseline will exist a column of oil. From the pickup tube 32 and the outermost extreme radius thereof to the annulus 34 as a baseline will define a column height of the heavier species 24 or phase 24, water. Thus, the pressure differential between the conduit 38 and the annulus 34 effectively defines, at any rotation of velocity, the column heights of the heavy and light columns, and therefore defines the position of the dispersion band 30.

To move the dispersion band 30, one may manipulate the backpressure, such as by constricting the flow from the conduit 38 until a desired pressure differential is reached, characterizing and reflecting a specific set of column heights. The corresponding radius 50 is thereby achieved.

Referring to FIG. 10, the pressure differential, or the pressure addition that should be added to the conduit 38 carrying the lighter phase 26 from the shell 12 is defined. It is defined in terms of comparative densities, and the radii of the interface 30 or dispersion band 30, and the location of the radius $R_4$ 48 illustrated in FIG. 1.

Looking at the centrifugal or centripetal forces, each of the columns actually exists with a minimum pressure near its respective outlet 34, 38, and a maximum pressure at a maximum distance 44, 50, or radius 44, 50, respectively, away therefrom. Thus, the oil column exists with its bottommost, highest pressure, at the dispersion band 30. Its lowest pressure is at the top of its oil column, the centerline 40 at the center at the conduit 38 discharging 77 that species 26. Meanwhile, the water column has its maximum value pressure at a maximum radius 44 of the cavity 20 of the shell 12. Meanwhile, the lowest or lightest head value will exist at the centermost position, closest to the center line 40, the innermost surface of the annulus 34 discharging 78 the heavy species 24.

Figure 11:
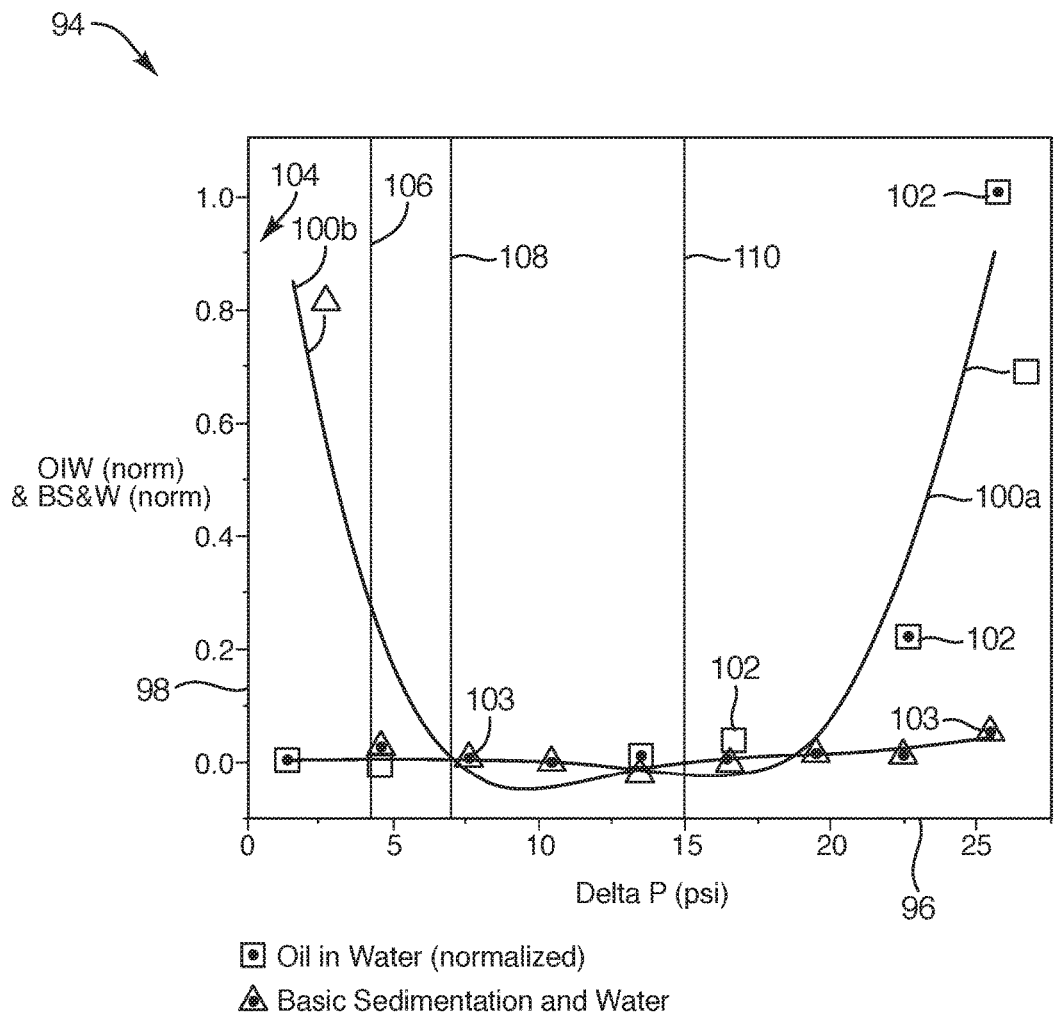
FIG. 11 is a chart illustrating data points and a curve fit of those data points of a value (normalized) of the oil in water concentration as a function of the delta (difference) in pressure or pressure differential between the output lines, and a curve of the basic sediments and water concentration (normalized) in the oil phase or species exiting an experimental separator in accordance with the invention.

Referring to FIG. 11, an experiment in accordance with the process 82 resulted in the chart 94. An x-axis 96 reflects the delta p 96 or pressure differential 96. The y-axis 98 reflects a normalized fraction 98 of the contaminant in either one of the separated species 24, 26. Thus, the curve 100*a* represents the fraction of oil in water, where water is the separated bulk heavy phase 24. Meanwhile, the curve 100*b* represents the water and basic sediments as a fraction of the oil as a light phase 26 separated in the system 10.

In the illustrated experimental data 102, the various data points 102 reflect the oil fraction remaining in separated water 24 or the heavy phase 24. The data points 104 represent the water in basic solids or sediments remaining in the oil 26 or light phase 26. One will note that the curves 100*a*, 100*b* fitted to the respective data points 102, 104 each provide a minimum value.

In the experiments, various set points for the pressure differential 96 remain. For example, the line 105 represents a delta p 96 or pressure differential 96 at which the residence times of both species 24, 26 were equal to one another.

The experiments began with a set point corresponding to the line 108. This line 108 reflects the maximization of settling area according to settling theory. The curves 100 (where the trailing letter represents a specific instance of the item identified by the reference numeral) both remained monotonic, not yet having a minimum.

After using the pressure differential 96 corresponding to the line 108 at which the settling area was maximized in the system 10, the experimental procedure shifted the pressure differential 96 to a value 106 corresponding to the line 106 where residence times are equalized for the heavy 24 and light 26 phases. Rather than improving or minimizing the amount of contaminant (opposite phase) in each of the separated phases 24, 26, the separation performance was worse. The purities were highly compromised, and the system performance was moving farther away from a minimum of impurities.

The experiment was shifted to cast about for other relationships that might be characterized or equalized or even set in a particular ratio between the phases 24, 26. The concept of equalizing settling distances was hypothesized as one way to seek or test for an optimum. The line 110 represents a value of the pressure differential 96 at which the settling distances 66*a*, 66*b* were equalized with one another.

Notwithstanding that the contaminants are not at their absolute minimum values according to either of the curves 100*a*, 100*b*, the equalization of settling lengths, as illustrated by the line 110, does produce a value that is robust, insensitive to small changes in operation, and still remains well within an operational range of acceptability of the minimum possible value of contaminants.

Thus, minimizing contaminants, as a dependent parameter to be selected 83, is now available. Moreover, stability around that set point will not be taxed to maintain a stable solution. This promised a method for optimizing the purity or the effectiveness of the separation of species 24, 26 according to a theory of the invention.

Note from FIG. 11, that the actual pressure differential 96 or value 96 of pressure differential at which each of the species 24, 26 should be set to obtain its minimum of contaminants may be different. However, the matching of the settlement distances at the line 110 provides a suitably close value for both species 24, 26. Neither is sacrificed for the other.

Thus, in a system, apparatus, and method in accordance with the invention, the equalization of the settling lengths 66*a*, 66*b* of the respective species 24, 26 separating out of their opposite species 26, 24 appears to provide an optimization for both species simultaneously, heretofore unconsidered, let alone achievable. In fact, in prior art systems, operation intended to focus on one species or the other. The concept of optimizing both simultaneously is a result unique and unexpected in the instant situation and the instant invention.

Figure 12:
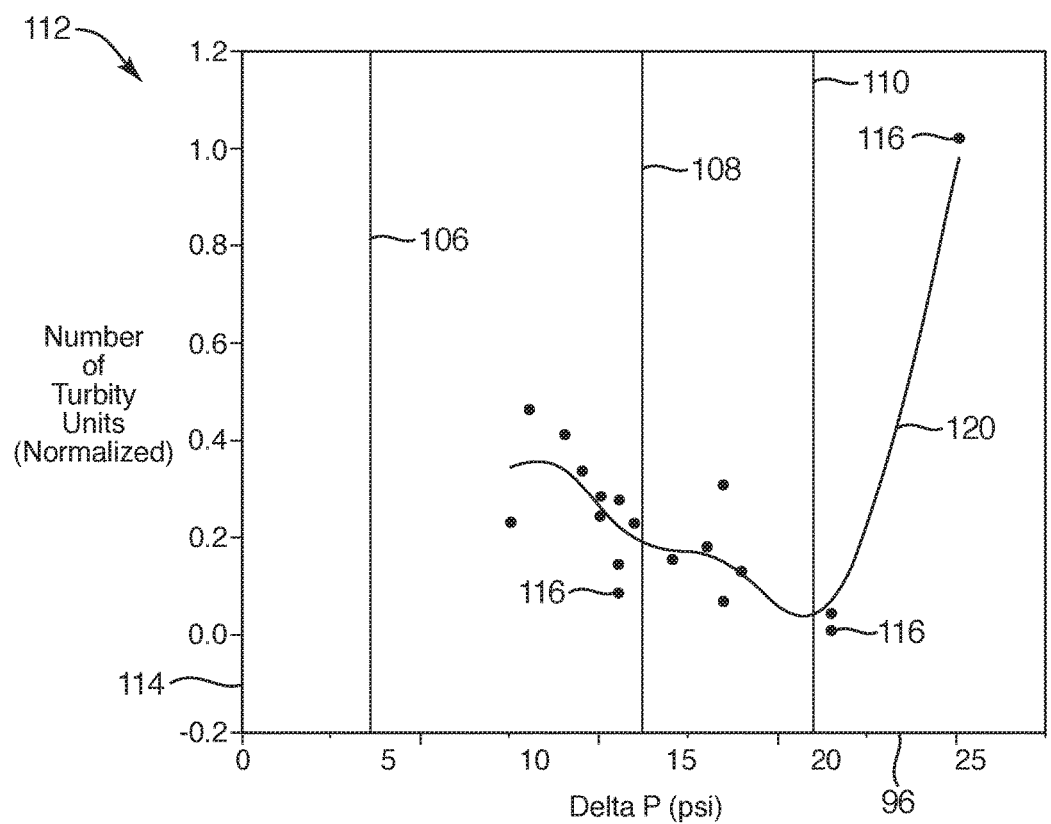
FIG. 12 is a chart plotting the number of turbidity units (normalized) as determined by a light scattering test as a function of the delta p or pressure differential between the effluent lines of heavy and light phases, in the heavy (water in this case) effluent from an experiment in a separator system in accordance with the invention.

Referring to FIG. 12, data from a series of experiments is illustrated in a chart 112 in which the x-axis 96 represents the differential pressure 96 as an independent variable. The net number of turbidity units 114 (normalized) is illustrated on the y-axis 114. Each of the data points 116 represents a value of the NTU or number of turbidity units. NTU is a method and value characterizing the impurities in a flow by a measurement of scattering of light through the bulk medium as a result of the index of refraction change between phases 24, 26 and reflecting or scattering of light by the impurities therein.

In the illustrated embodiment, the curve 120 represents the fit to the data points 116. One will note that in this data, the maximum settling area represented by the line 108 is accomplished at the value of the differential pressure 96 illustrated. The line 106 reflects a value of the pressure differential 96 when set to equalize residence times. Meanwhile, the settling distance equalization represented by the line 110 provides a virtually perfect match for the minimum turbidity in the measured sample.

When looking at the water or heavier species 24 in this experiment, optimization is shown to approach an excellent match with the equalization of settling distance between species 24, 26. Thus, the experiments prove out that this particular parameterization for control of a system 10 in accordance with the invention works and meets the need to be able to optimize a purification parameter.

Figure 13:
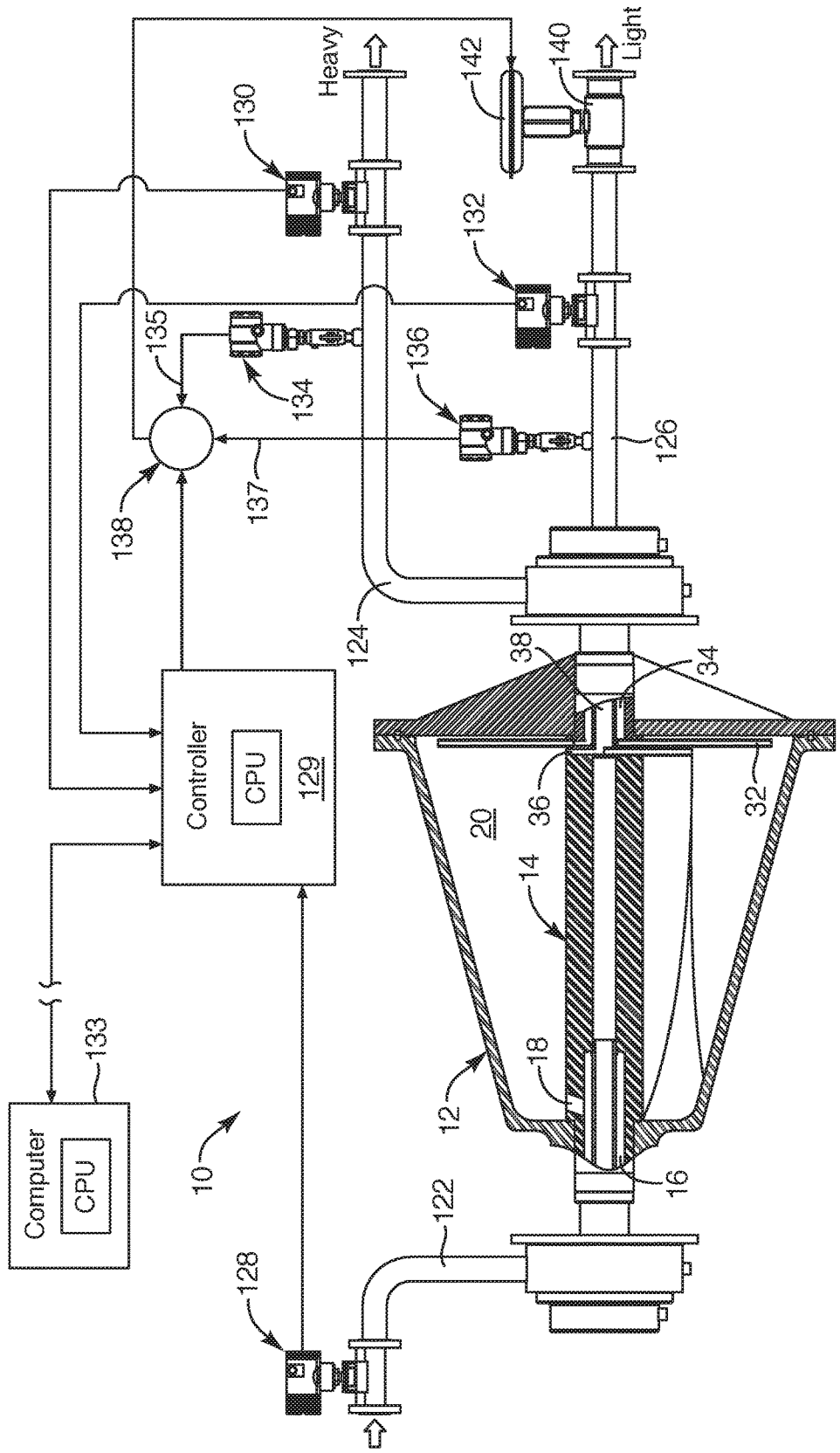
FIG. 13 is a side elevation view of a simplified illustration of a separator in accordance with the invention equipped with a system of flow meters and pressure sensors, as well as a control loop controlling a control valve establishing back pressure on a light species effluent line exiting a rotating separator in accordance with the invention.

Referring to FIG. 13, a system 10 in accordance with the invention may be set up to provide for automatic feedback control to optimize a desired parameter. For example, in the illustrated embodiment, an influent line 122 into a shell 12 may be monitored by a flow meter 128 reporting data to a controller 129 having a processor. The controller may report to and be programmed through a remote computer 133.

Meanwhile, an effluent line 124 may be monitored by a flow meter 130, while an effluent line 126 may be monitored by its corresponding flow meter 132. These flow meters permit online measurement of the cut fraction of each species compared to the influent flow 22 passing by the flow meter 128 and influent line 122.

A sensor 134 senses and reports pressure in the line 124 of the heavier species 24. Likewise, a pressure transducer or device 136 on the line 126 provides data reporting the pressure in the affluent of the lighter species 26. A line 135 feeds data from the sensor 134 to a comparator 138. Similarly, the line 137 feeds data from the sensor 136 to the comparator 138. The controller 129 may control a set point for the comparator 138 to follow. The comparator 138 thereby sends a signal to a drive 142 controlling a control valve 140. Backpressure on the line 126 may be adjusted according to a pressure differential measured and maintained by this control loop. The actuator 142 or drive 142 may be of any particular type, and the bandwidth need not necessarily be particularly high. For example, the bandwidths on the order of measuring every thirty seconds or two per minute have been shown to be adequate for the experiments conducted. Thus, the control hardware need not be sophisticated nor excessively precise, nor particularly rapid, in order to maintain the system 10 in an optimized condition.

Figure 14:
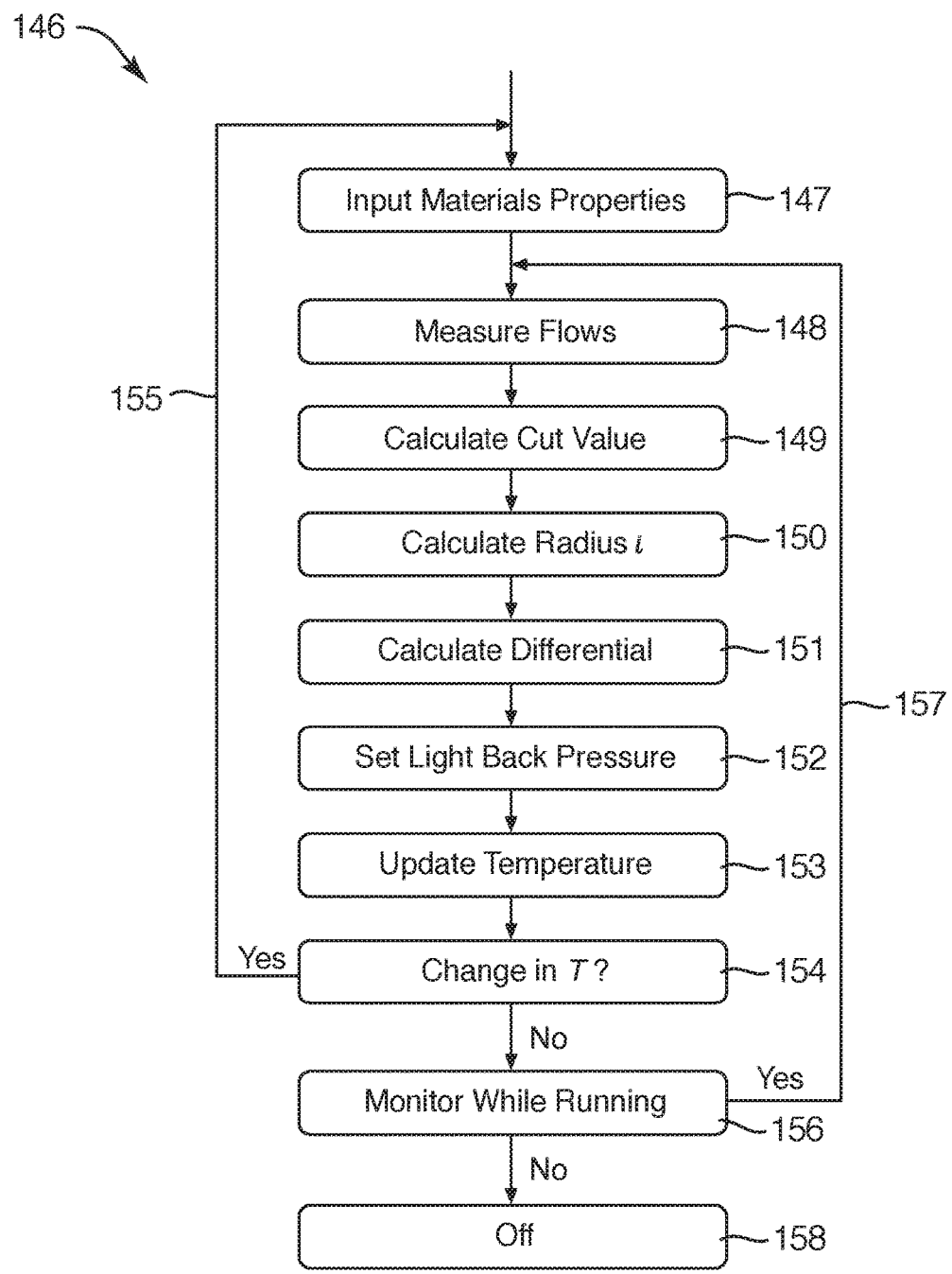
FIG. 14 is a schematic block diagram of an optimization process for optimizing and controlling the dispersion band radius by controlling the backpressure, as a function of the material properties, temperature, and constituent fraction (cut value) of an incoming stream to be separated by an apparatus and method in accordance with the invention.

Referring to FIG. 14, a process 146 for optimization in accordance with the invention may provide inputting 147 material properties of the materials or fluids mixed together in the influent 22. Thereafter, measuring 148 the flows 57a, 57b of the species 26, 24 may provide the ability to calculate 149 the cut value for each. Accordingly, one may calculate 150 in accordance with the equations and principles described hereinabove the radius 50 at which the dispersion band 30 should be set.

The computer 133, the controller 129, or both may execute in accordance with the equations and principles described hereinabove, to calculate 151 the differential pressure 96 required to obtain the radius 50 for the positioning of the dispersion band 30. The controller 129, computer 133, or both may execute to set 152 the back pressure to be maintained by the valve 142 on the light phase thereby. The system 10 and computer 133 may periodically update 153 the temperature of the influent 22, since material properties will be dependent thereon. Testing 154 any change in temperature may report any change, resulting in a return 155 to a recalculation and inputting 147 by the computer 133, controller 129, or both the material properties.

If the material itself is changed, then material property changes are required. If the temperature has not changed, according to the test 154, then monitoring 156 may continue while running, with periodic measurements taken, and corresponding adjustments made.

For example, a return 157 from the test 156 results in measuring 148 again each of the flows in the lines 124, 126 passing through the flow meters 130, 132. A processor in the controller 129, computer 133, or both may recalculate 149 cut values, and complete the process 146 in a repeating manner. Ultimately, the monitoring 156 is best conducted continuously at a periodic frequency as long as the system 10 is operational. Otherwise, the system 10 may be shut off 158 for specific service requiring or warranting a shut down.

Figure 15:
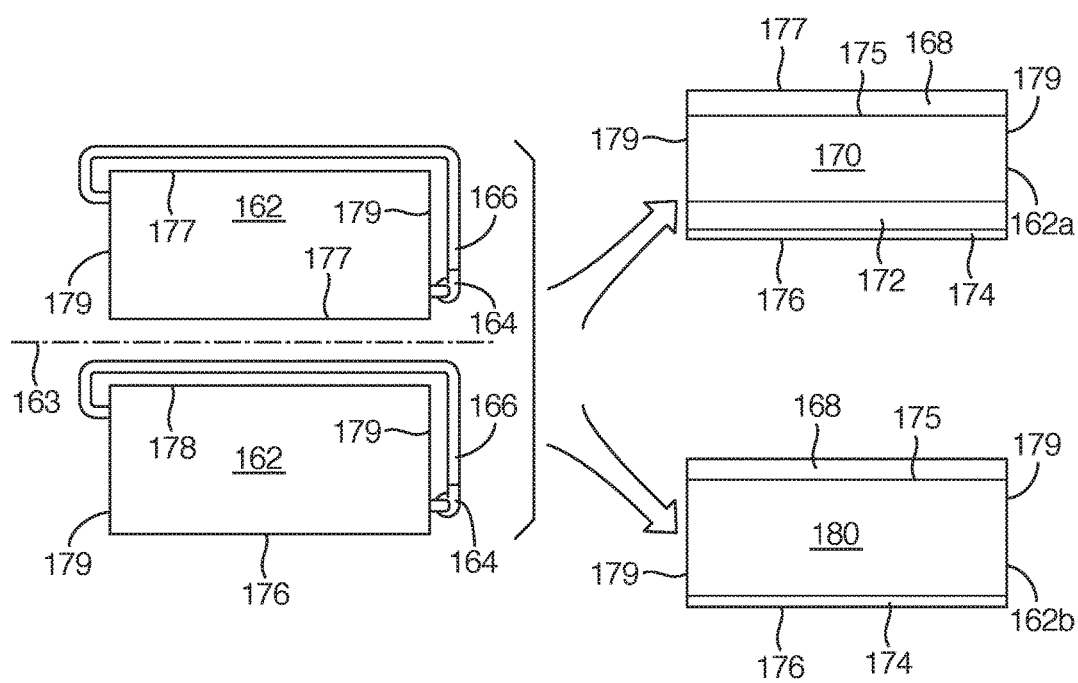
FIG. 15 is a schematic view of the top and side aspects of a tank for holding production oil or slop oil in accordance with the invention.

Referring to FIG. 15, while continuing to refer generally to FIGS. 1 through 21, a process system 160 involves a tank 162. Typically, a tank 162 may be repurposed from a fracturing fluid holding tank (frac tank) such as a tank trailer used in various production processes, and ubiquitous within a producing oil field. Such a tank trailer and a transfer system (fill, drain, clean) system is described in U.S. Provisional Patent Applications 62/208,945 and 62/259,856, both hereby incorporated herein by reference.

In one currently contemplated embodiment, such a tank 162 may be fitted with a pump 164, drawing from an output near the bottom of the content and pumping into the tank 162 at the most distant upper corner. Between the outlet and the inlet, a line 166 or roll line 166 may contain or connect to the pump 164. The roll line 166 draws from low in the tank 162, passing the content to the pump 164, which pressurizes the flow. Accordingly, the pump 164 increases the pressure in the roll line 166 and delivers the content through an upper corner or inlet of the roll line 166 into the tank 162.

At the top of the tank 162 is effectively a space 168 or air 168. The air 168 is typically sealed into the tank 162, because it contains volatile organic compounds, such as light weight species or constituents of crude oil. Below the gap 168 or air 168 is oil 170. However, exactly how that oil 170 is distributed, along with its fraction of water 172 is central to the point of the instant invention.

For example, if a tank 162a is suitable for transport to a processing facility or refinery, then the space 168 or air 168 at the top will cover a layer of oil 170, which itself overlies a layer 172 of water 172. Meanwhile, basic sediments and water introduced into the tank 162 may further separate to leave a layer of sludge 174 containing high molecular weight hydrocarbons, some amount of water, and a comparatively large fraction of basic sediments. Basic sediments and water, abbreviated as BS&W, will typically involve a large fraction of clay, and possibly silicates, such as fines from the sand of a rock formation.

If the oil introduced into a tank 162 is of a condition or quality that does readily separate, as illustrated in the tank 162a, it may do so, being drawn off for sale. Otherwise, it falls into the category or characterization of the tank 162b. In the tank 162b, a distinct separation between the layers 170, 172, 174 does not actually exist. To some extent, the increased density of sediments or basic sediments may still accumulate as sludge 174 along the floor 176 of a tank 162. However, most of the content 180 is actually characterized as a quasi homogeneous mixture 180 engaged in a very slow (inadequate) process of separation.

In other words, the mixture 180 in the tank 162b contains mixed oil, water, and sediments characterized by gradients. By gradients is meant that a fraction or portion (e.g., a percentage) of the mixture 180 constituted by each of the principal constituents (oil 170, water 172, sediments 174 or sludge 174) varies between the drain line 166 near the floor 176 and the liquid level 175 near the top 177 or ceiling 177 of the tank 162b.

As a practical matter, the fact that the gradient mixture 180 is still quasi homogenous, that is all constituents are present at virtually all levels, is not well understood in the art. When such tanks 162b are sampled and tested, their contents may be centrifuged to separate, in order to establish exactly what percentages of the individual constituents 170, 172, 174 exist.

However, the action of gravity is inadequate to actually accomplish this same separation in any reasonable amount of time. The centrifuge relies on intense acceleration, solvents, and heat. The content of the centrifuge, and thus the mixture 180 of the tank 162, are not constituted the same as any of the layers in the tank 162a.

The ultimate destination of the content of a tank 162a is typically a refinery, for the oil 170. The water 172 may go to a reinjection site. It may be further processed before being evaporated in a pond, reinjected into a well, reused as a constituent such as for fracking, or the like.

Meanwhile, the mixture 180 in the tank 162b has a host of options, none of which is entirely satisfactory. Depending on the price of oil, such a content 180 may be left in the tank 162b, and set aside to continue settling or dividing under the influence of gravity as a separator for a long period, such as a month or more. It also occupies a certain amount of real estate, to say nothing of requiring the tank 162, which should have been reused in approximately two day cycles. Thus, the capital investment for holding that content 180 is substantial.

Moreover, chemical decomposition may occur partly because of chemistry of the material 180, but also due to biological attack. This may cause degradation of the oil chemically. The good and bad news of biological attack is that microbes exist that do break down oil. This is good news for oil spills in the environment. However, such biological activity also occurs in standing oil in a tank 162b.

Thus, if the price of oil is sufficiently high, the content 180, slop oil 180, may be further settled, with the best constituents, any oil 170 that appears at the top over some extensive period of time, being sent to refinery. Meanwhile, the remainder must be sent to some other use, such as for use in asphalt compounding, or the like. For such applications, the oil value is reduced further than it already was by the presence of sediments. Ultimately, asphalt is going to be used in applications where sediments are an asset rather than liability. However, such slop oil will sell at much at very discounted rates, such as half of crude oil meeting a market specification.

At its worst, the content 180 may be too poor in quality, and non-separable in a reasonable amount of time. Meanwhile, a shortened amount of time may be forced upon an owner by other conditions, such as the lack of real estate, lack of extra tank trailers 162, the lack of equipment, the lack of a ready market, or the like. Accordingly, the entire content 180 may be shipped to a use for asphalt.

There is at least one worse option, below the worst disposition by sale. That is having to pay a hauling company to transport the content 180 to some other location by some other facility, because there is not value sufficient to any other user to justify paying anything for the content 180.

Accordingly, a system and method in accordance with the invention provide a mechanism for returning the content 180, at least a fraction thereof, to oil within market specification. The remainder of the figures demonstrate certain of the steps in those processes.

Figure 16:
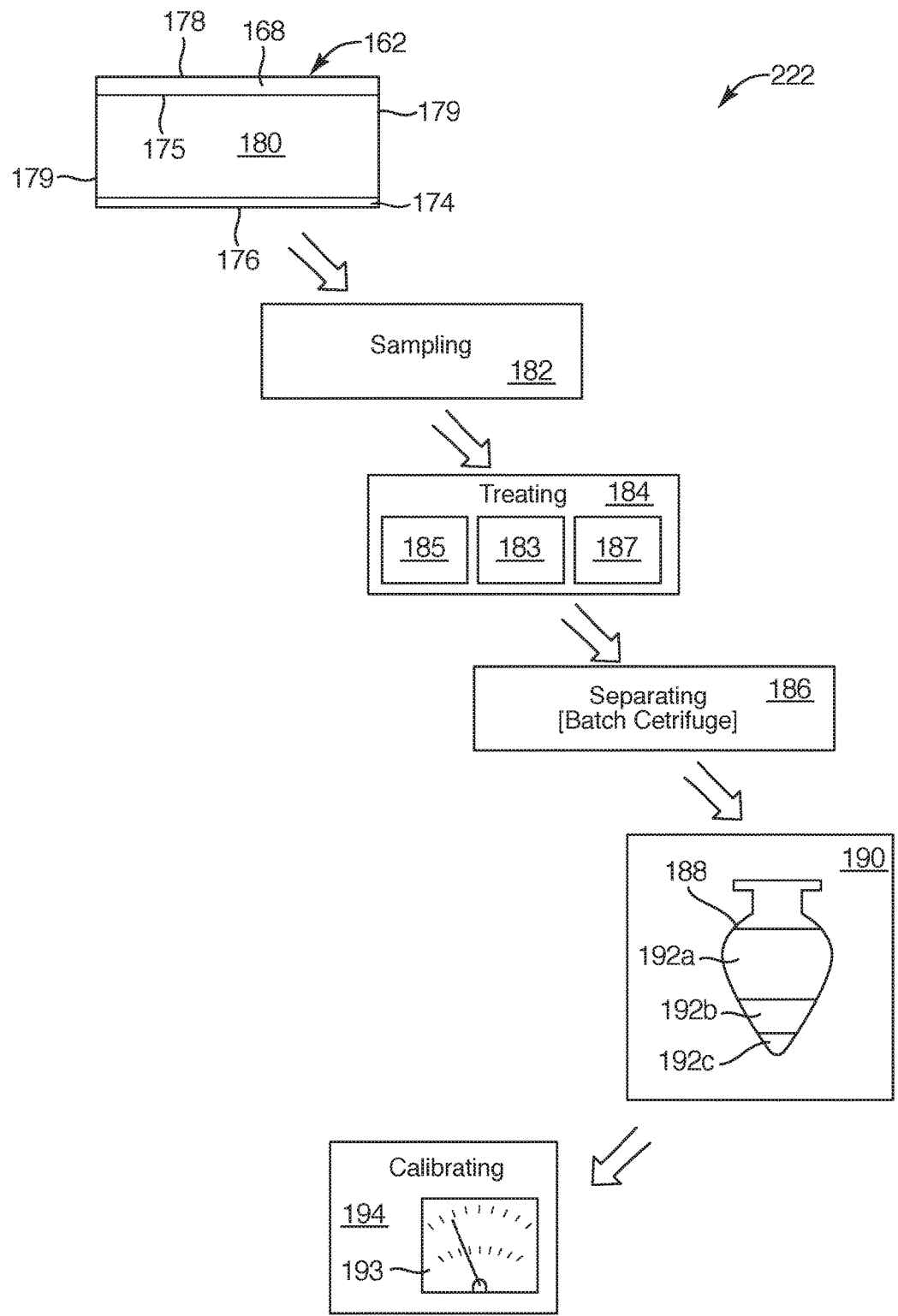
FIG. 16 is a schematic block diagram of a process for testing the content of such a tank and calibrating an in line basic sediments and water (BS&W) meter being used to monitor the outflow during draining of such a tank.

Referring to FIG. 16, a process 222 (see FIG. 19) for calibrating 194 a BS&W meter requires sampling 182 the content 180 in a tank 162. Typically, sampling 182 is done through a thief sample taken through a thief hatch at the top 178 of a tank 162. A device is lowered to extract a sample from the top near the liquid surface 175 of the content 180. Given the nature of oil, the best quality or the purest oil 170 will always be at the liquid level 175.

Following sampling 182, treating 184 the sample 185 of content 180 may involve application of heat and solvents to the sample 185. The sample 185 may also be mixed with one or more solvents 187. The benefit of heat and solvents 187 will be several. For example, heat will reduce viscosity of the material. Solvents 187 may do likewise. In addition, solvents 187 may break up mechanical and chemical bonds that may exist between oil and sediment.

In addition to solvents 187, de-emulsifiers may also be added in order to separate sediments from oil. Since emulsifiers may promote bonds between oil and water, de-emulsifiers may break those bonds and encourage separation of water and oil.

The importance of the process 184 of preparation 184 of a sample 185 is demonstrated in the centrifuge operation 186. Centrifuging 186 involves placing the sample 185 as modified in the preparation process 184 into a centrifuge tube 188. A centrifuge tube 188 is effectively a non-linear, graduated container. The cross-section of the line-symmetric, volume-of-revolution shape is illustrated by the centrifuge tube 188 in the figure.

The open end of the tube 188 is directed by centrifugal acceleration toward the axis of rotation of a centrifuge, while the closed point is directed at the maximum outer radius. The tubes 188 may actually be placed in a condition that they are canted or angled such that they will hold their contents. In certain sampling centrifuges, the tubes 188 may sit in sockets, which sockets rotate to a vertical orientation holding the contents in the tube 188 when loading and unloading, but swing into a plane of rotation upon sufficient speed of rotation of the centrifuge.

The result of centrifuging 186 the sample 184 in a tube 188 is separation into layers 192a, 192b, 192c. The layer 192a is the lightest, and is constituted as oil 192a (with solvent), the water 192b forms a middle layer 192b. The solids 192c or sediments 192c constitute the smallest and bottom most layer 192c of the constituents. A trailing reference letter indicates a specific instance of an item of that type identified by the number. Either use, of the number alone, or the number with the trailing letter, is proper. Both need not be mentioned.

Reading 190 is effectively a manual process. Markings on the tube 188 indicate volumetric lines at certain heights. Calculation of percentages or fractions will account for solvents or other additives. Accordingly, the volume of solids 192c can be determined and recorded, along with the volume of water 192b, and the volume of oil 192a. Together, these constituents constitute the sample 184 together with its additives.

For example, the solvents are typically distilled constituents of oil. They may simply mix homogenously with the oil 192a. Some constituents, may actually mix with the water 192b. Thus, one may calculate, typically with additives equal in volume to the volume of the sample 185, so that the BS&W, and the solids in particular, are in a tube 188 having more (typically by twice) the volume of the sample 185. Accordingly, the mathematics may be worked out to determine the percentage of water 192b and the percentage of solvents 192a in the sample 185.

Calibration 194 follows reading 190 of the volumes of the content 192. A reference numeral references a type or entire class of item. The calibration 194 may proceed. Typically, a calibration 194 involves zeroing the intercept of a curve or line that represents the graph of a particular property as a function of a percentage or fraction of BS&W content. For example, capacitance is a useful measure, and reflects linearly the water content in a sample 185. The curve is effectively a straight line in which capacitance is a function of water percentage.

Reading 195 into the process 194 the output of a BS&W meter may be done electronically. It may represent a voltage, or some other value. This number may be translated to a fraction of BS&W, a percentage of BS&W, a fraction of water, or the like. Typically, sediments have little effect on capacitance or other properties. Rather, water tends to affect capacitance most directly and detectably.

The reading 190 demonstrates the relationship between total volume of a sample 185, and its constituents 192a, 192b, 192c. However, relationships or ratios of those constituents 192 may then be used to presume from water content or calculate from water content, the exact amount of water and corresponding solids to be expected, based on the calibration process 194. A BS&W meter 193 may thus be calibrated 200 or reset 200 in consequence of an input of a reading 195 reflecting BS&W content actually achieved, and the corresponding capacitance or other property detected.

For example, an intercept comparison shows that an equation 196a reflects that a changing capacitance is proportional to a change in a percentage of water 192b in a sample 185. Similarly, a capacitance in the equation 196b as a letter $C_1$, represents a percentage of water in a condition 1 or first condition. This may, for example, be a set point for a BS&W meter 193. On the other hand, at a later time, a sample 185 tested by the process 222 illustrated may result in a second capacitance value or $C_2$ shown in the equation 196c. This value represents a different percentage of water.

Comparison of these two capacitances $C_1$, $C_2$ may demonstrate not only the water content, but also the effect of the oil itself. For example, actual oil 192a in a mixture 180 may vary somewhat in chemical consistency. Such differences may affect the apparent capacitance. However, it has been found experimentally that capacitance variation changes with water, and thus the slope is reliably reflected by, or reliably reflects, water content.

Meanwhile, calibration values found in the equations 196 reflect the intercept of such a graph, where the slope remains controlled by changes therein. Accordingly, the equation 196d reflects the test for capacitance ($C_{TOP}$) in which a tank then has a minimum percentage of water, or the sample 185 of the mixture 180 has the minimum quantity of water. Thus, this serves as a set point for the comparison 198 and consequent calibration 200 or reset 200 of the BS&W meter 193.

Figure 17:
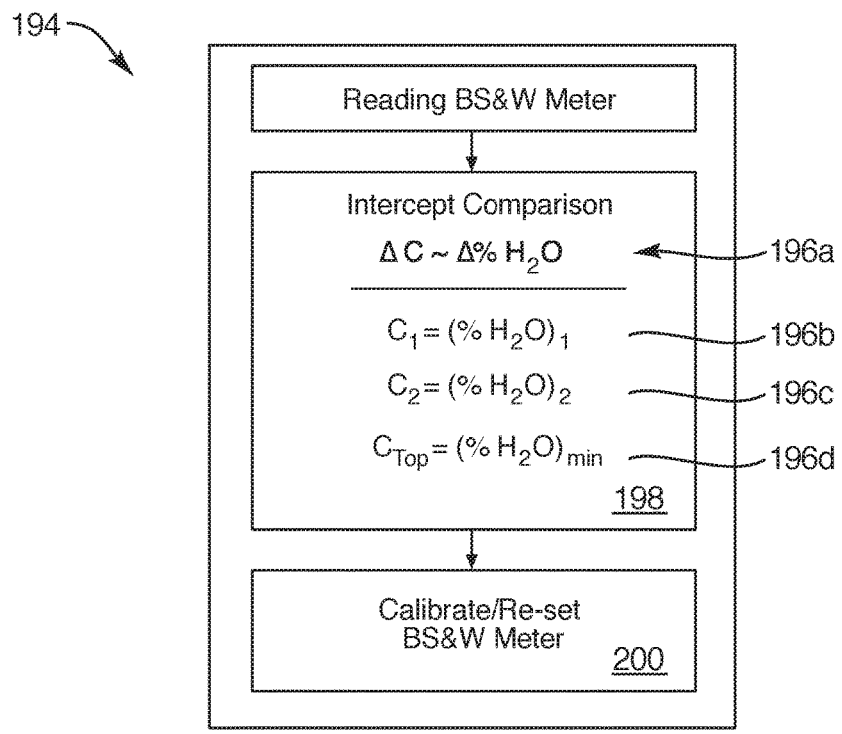
FIG. 17 is a schematic block diagram of a process for calibrating such an in line BS&W meter.
Figure 18:
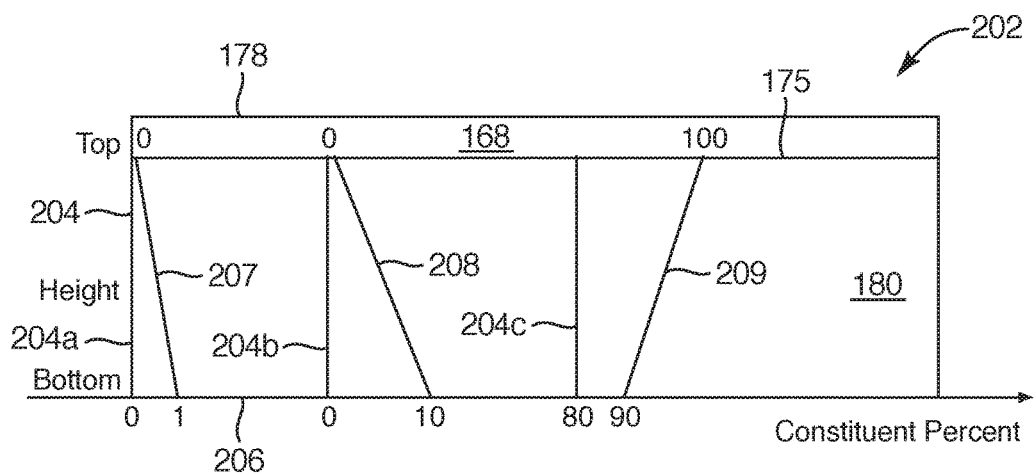
FIG. 18 is a chart illustrating graphically the height of a tank on one axis, and illustrating a percentage of various constituents on another axis, each referenced to a datum.

Referring to FIG. 18, while continuing to refer generally to FIGS. 1 through 21, a graph 202 illustrates a height axis 203 corresponding to the height or altitude of the liquid level 175 away from the floor 176 of a tank 162. Meanwhile, a percent axis 206 is illustrated horizontally. The percent axis 206 has periodic datum lines 204, such as the lines 204a, 204b, 204c. Accordingly, each graph 207, 208, 209 represents a value along the axis 206 (e.g., a percentage) with respect to the corresponding datum 204a, 204b, 204c.

One may see that the solids curve 207 or line 207 typically ranges down to a percentage of about zero at the liquid level 175 near the top 178 of a tank 162. It will typically range up as high as about one percent or perhaps up to three percent near the bottom 176 of a tank 162, at the top of the sludge layer 174.

Similarly, the percentage of water 172 shown by the line 208 varies between about zero percent at the liquid level 175, and rises to about ten percent near the bottom 176 of a tank 162. Finally, the percentage of oil illustrated by the line 209 or curve 209 varies from a value of about 100 percent at the liquid level 175, and decreases to about the amount of BS&W, leaving a value of about 90 percent oil near top of the sludge 174 at the bottom 176.

A major significance of FIG. 18 is to demonstrate that the quasi-homogenous content 180 of FIG. 15 contains, effectively, all constituents at all levels. The percentages of constituents 192a, 192b, 193c varies along the height axis 204, but does not necessarily exclude any constituent 192a, 192b, 192c at any point. In fact, this is the nature of slop oil 180. It is not readily separable into its constituents 192 in a day or two of gravity (a reasonable time).

Figure 19:
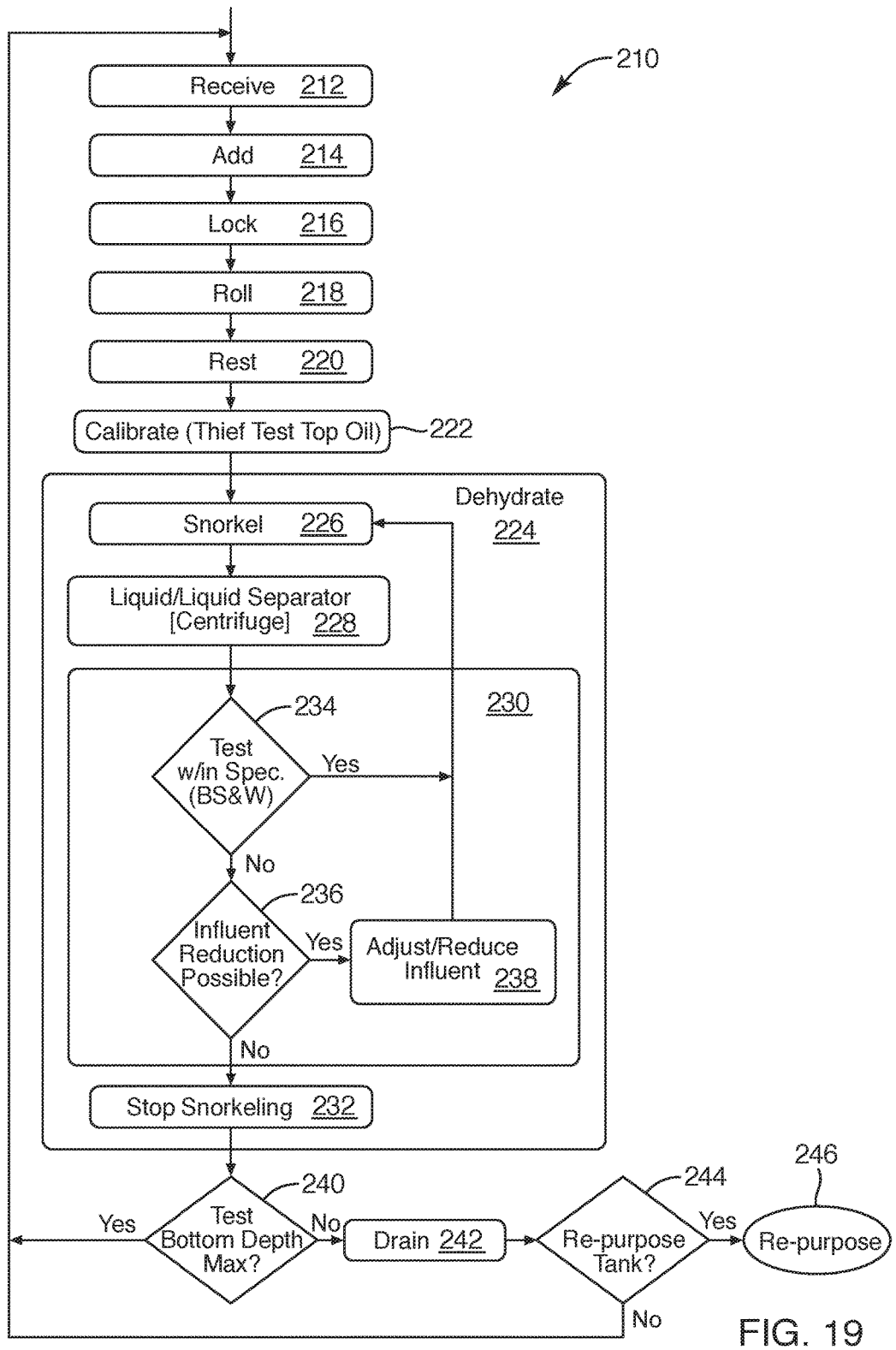
FIG. 19 is a schematic block diagram of a process of operation of an oil tank system in accordance to the invention.

Referring to FIG. 19, while continuing to refer generally to FIGS. 1 through 21, a control process 210 may begin by receiving 212 the content 180 in a tank 162. Various chemicals added 214 may include emulsion breakers, sludge treatments, biocides to combat activity of bacteria, and the like. The various chemicals added 214 represent attempts to salvage economically, by dehydration, the highest quality and the most oil 170 from the content 180. Following filling, a tank 162 is closed 216 or locked 216 and rolled 218. Rolling 218 refers to mixing, not literal rolling the tank 162. Flow is passed from an outlet near one lower corner toward an inlet near an extreme opposite upper corner in order to promote flow and mixing throughout the tank 162.

Following rolling 218, resting 220 refers to a period of inactivity. Constituents 170, 172, 174 are permitted time to separate under the influence of gravity. Whether they will determines the need for these processes 210.

The rolling process 218 mixes in the additives or chemicals added 214 to the mixture 180 in the tank 162. Rolling 218 assures intimate chemical contact necessary between the chemicals and the mixture 180 to promote maximum effectiveness, maximum concentrations, and maximum proximity of those chemicals to the subject material 180.

By the same token, resting 220 promotes or permits the ongoing processes of chemical reaction. The additives 214 need time to work. The resting process 220 or step 220 provides the time required for chemical diffusion processes to transport mass to locations where it is needed on a molecular level.

For example, in the fields of chemical engineering and thermal engineering, the transfers of heat and mass in quiescent materials are diffusion processes. Fick's law of diffusion governs, in which the rate of mass transport is proportional to some constant depending upon the chemistry involved multiplied by a concentration gradient or difference in concentration between a source and a destination of mass transport. Similarly, the thermal equation shows that heat transfer is equal to some constant representing heat transfer coefficients, thermal conductivities, or the like multiplied by a temperature difference or a gradient in temperature through a distance.

A calibration 222 involves more than the process 194 of FIG. 17. For example, the process 222 is illustrated in considerable detail in FIG. 16. That is, sampling 182 must be done, followed by treating 184 the sample 185, separating 186 (typically by a centrifuge), and ultimately reading 190 the centrifuged 186 sample in its centrifuge tube 188 or non-linear graduated cylinder 188. Ultimately, calibrating 194 results in adjusting the BS&W meter 193 to move the intercept of a graph that provides an electrical property, such as capacitance as a linear function of a percentage 206 of water 208 in the mixture 180.

Ultimately, following an overall calibration process 222, dehydration 224 may commence. Dehydration 224 is initiated by drawing 226, typically by snorkeling 226, a portion of the content 180 from the tank 162. The withdrawal 226 or snorkeling 226 is preferably done as close to the liquid level 175 as possible. This assures that the maximum quality (minimum percent of BS&W) exists in the material withdrawn 226.

The withdrawn content 180 is then separated 228, in a liquid-liquid separator such as a centrifuge 12. The term or label of the centrifuge is placed in square brackets indicating that this is optional. Similarly, brackets in other schematic diagrams indicate options.

Once the separation 228 has occurred, the automatic process control 230 occurs. The control process 230 involves testing 234 with an in line BS&W meter 193, the content discharged from centrifuging 228. The test 234 finds whether the water content or BS&W content of the withdrawn 226 material 180 is sufficiently low. Then the test 234 reports that the output is of adequate quality. That affirmative answer results in a return to or a continuation of snorkeling 226 to remove 226 content 180 from the tank 162.

On the other hand, if the test 234 reports that the oil is no longer within specification, all is not lost. The process 210 need not stop. Rather, it has been found that a centrifuge 12 in accordance with the invention is capable of reducing 238 or adjusting 238 the flow of influent 122 into the centrifuge 12. A test 236 determines whether an influent reduction 238 or adjustment 238 is possible. The test 236 determines whether further reduction is within the operational rating of the transport equipment. Such equipment as a pump 256 (see FIG. 20) or a variable control valve 258 (also see FIG. 20).

If the test 236 determines in the affirmative that further reduction 238 is still within the operational parameters of the pump 256 or the control valve 258, then flow is adjusting 238 downward. This may occur by reducing 238 the flow through the pump 256, flow valve 258, or both. Meanwhile, the process 230 continues the snorkeling 226 to drain 226 the content 180 of the tank 162.

Ultimately, the test 236 will fail, or return a negative result. The discharge 260 or output 260 of the centrifuge 12 cannot obtain sufficient dwell time to be within specification. Snorkeling 226 must cease 232. At this point, the remaining content 180 must be disposed of in some other manner.

The test 240 determines whether the depth of the bottoms 174 or sludge 174 on the floor 176 of the tank 162 exceeds or falls short of a maximum depth. For example, at some point, the buildup of sludge 174 will interfere with the operation of the pump 164 during the rolling process 218. The test 240 does not include any residual oil that does not meet specification. That oil may be disposed of in some other way, typically with further processing, as discussed hereinabove.

Ultimately, however, after all saleable or useful oil of any category has been removed, the sludge 174 is tested 240 to determine whether it will interfere. Is the level yet below a maximum permissible, permitted by operation of the pump 164 and accessed by the line 166 during the rolling 218 step or process 218? If the test 240 results in a negative answer, the height of the sludge 174 is no longer below the maximum permissible. Draining 242, by whatever mechanism may be available, is required.

As discussed in the references incorporated hereinabove by reference, an annular snorkel system may drain sludge 174 through the same tank port shared with a coaxial snorkel drain line. Those details will not be repeated here, since they are already incorporated by reference.

After the tank 162 has been drained 242 or cleaned 242, a test 244 determines the disposition of the tank 162. If it is to be repurposed 246 then that will be done. Otherwise, the test 244 determines that the tank 162 will not repurposed, and will be returned to service. This results in filling 212 by or receiving 212 a new batch of content 180, with continuation of the process 210.

Thus, the test 234, to determine whether the oil remains within specification, the test 236 to determine if influent 260 or tank influent representing the output 260 of a centrifuge 12, may still be adjusted 238, and the test 240 determining whether the depth of sludge 174 is still below a maximum permissible, all permit the process 210 to continue. At the point that any of these tests 234, 236, 240 results in a negative response, then the respective process 230, 210 is halted, and procedures are diverted as illustrated.

Figure 20:
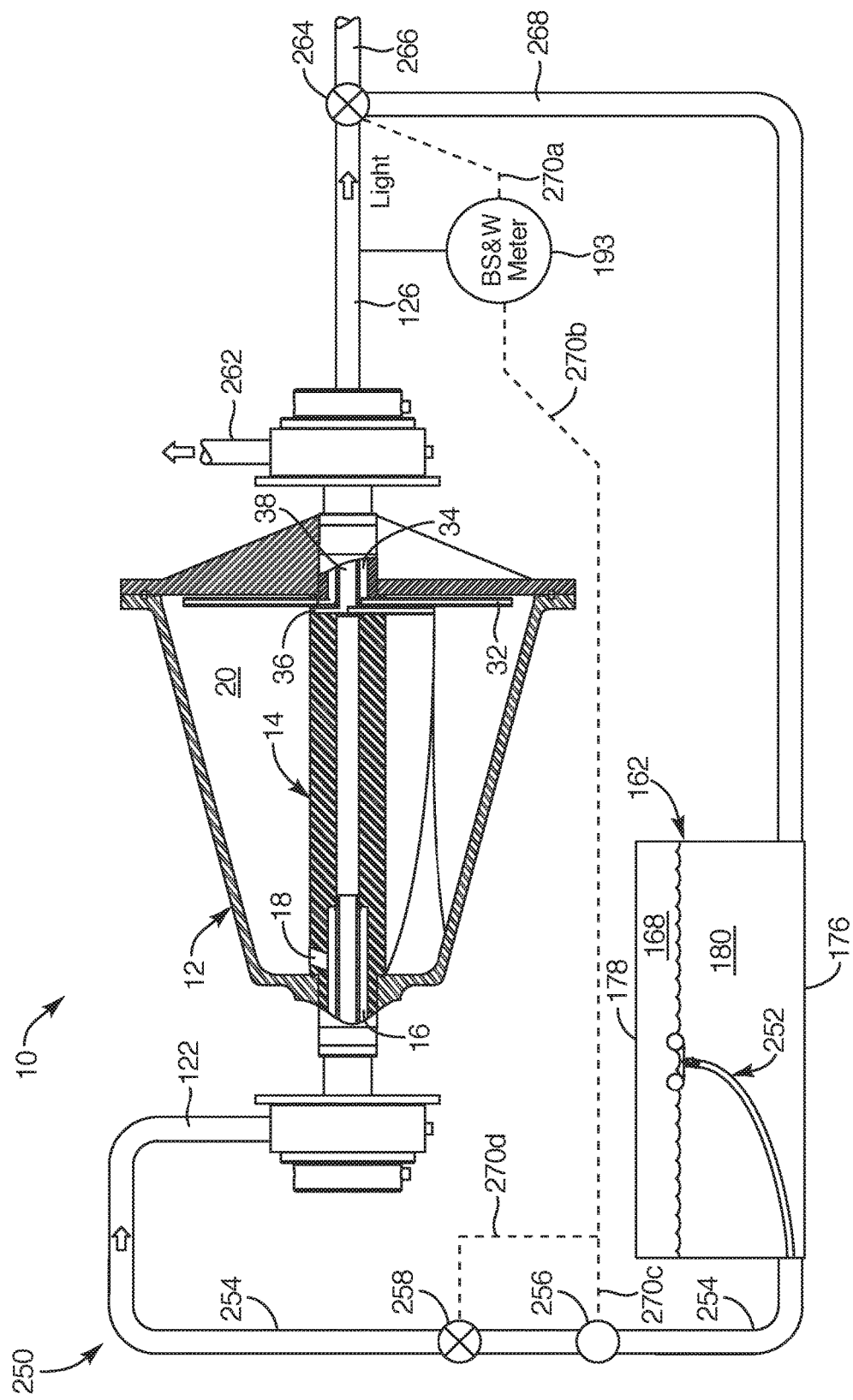
FIG. 20 is a schematic block diagram of one embodiment of a separator system with suitable controls for implementing an optimization process for assuring that all content removed from a tank remains within a predetermined specification for quality, relative to BS&W content.
Figure 21:
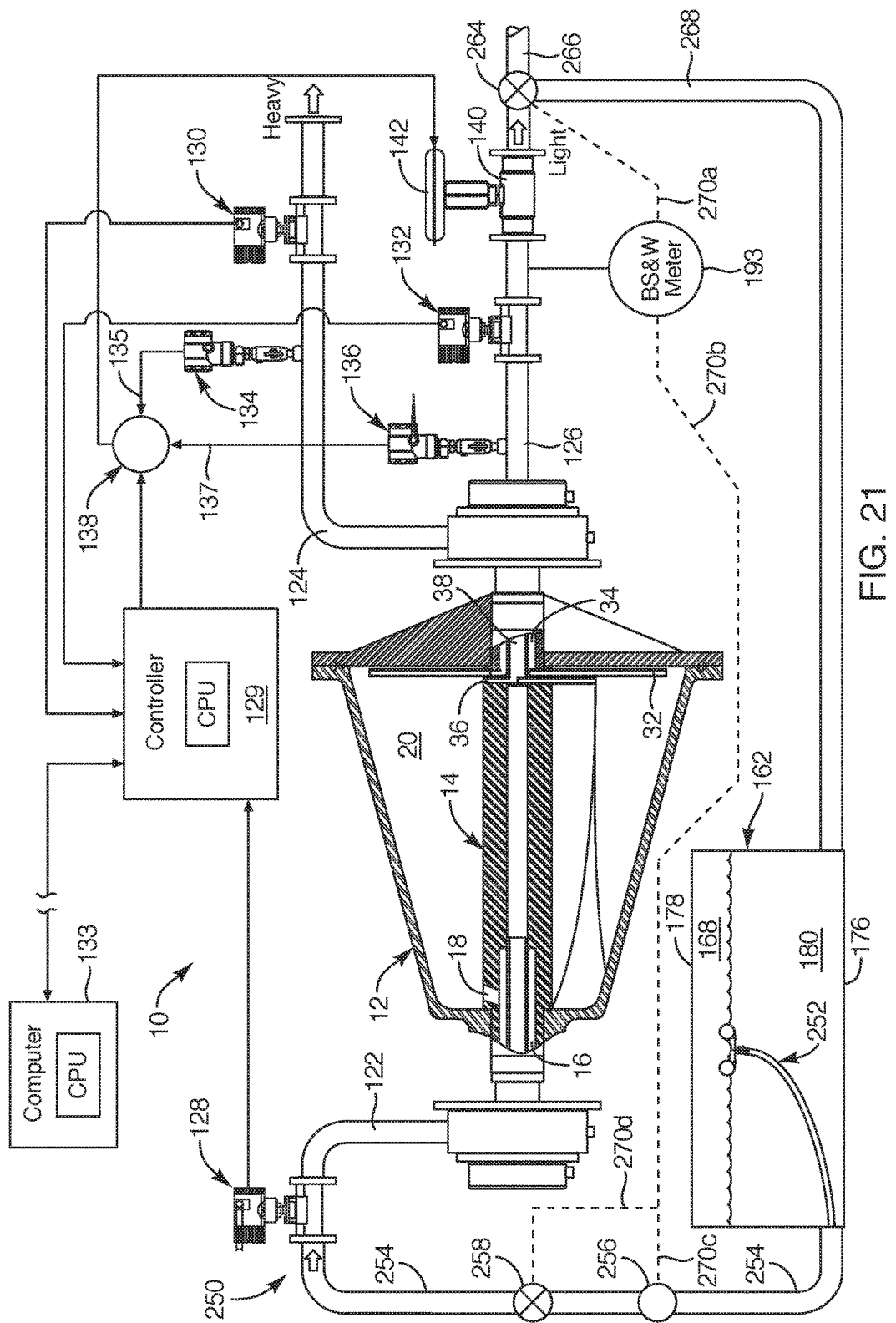
FIG. 21 is a schematic block diagram of such a system, combined with a control mechanism for controlling the radius of the dispersion band of a processed liquid (e.g., oil to be dehydrated) in accordance with the invention.

Referring to FIGS. 20 and 21, while continuing to refer generally to FIGS. 1 through 21, a trim controlled separator system 250 centers around a centrifuge 12 as described in detail hereinabove. The embodiment of FIG. 21 includes the processes described hereinabove for matching settling distances of constituents within a centrifuge 12 by variation of the pressure differential between the output lines 124, 126. However, that balancing process is not required for the trim control process 250.

Referring to FIG. 20, a trim controlled separator process 250 may include a drain 252 or snorkel 252 accessing a mixture 180 contained in a tank 162. Again, the details of the snorkel 252 are contained in the references incorporated hereinabove by reference. The snorkel 252 drains into a line 254 or feeds a line 254 serviced by a pump 256. The pump 256 pushes the content 180 retrieved through the snorkel 252 through a line 254 into the centrifuge 12. A control valve 258 or flow control valve 258 may be placed in the line 254 downstream from the pump 256.

In other embodiments, a pump 256 may be used alone. For example, a variable speed pump 256, or any other type of variable output pump 256 may be used. Ultimately, the function of the pump 256, control valve 258, or both, is the control over the adjustment 238 of influent 122 passing into the centrifuge 12. By controlling the influent 122, the output 260 will be similarly reduced, but the result will be an output flow 260 that is fully within any specification demanded by a market quotation.

The light flow 260 or light species 260, compared to the heavy species 262 (typically water) is monitored by a BS&W meter 193 in line with the line 126. The BS&W meter 193 has been described in some detail, indicating a capacitance meter 193 having sufficient software logic to relate capacitance change to a change in BS&W, actually water, as a constituent 192 in the material 180. The BS&W meter 193 provides feedback information and may operate as a controller on three devices 256, 258, 264.

At first glance, this may seem like a violation of control theory. However, the diverter valve 264 is simply a cutoff or shutdown device 264. It does not seek to proportionally control flow or the process 250. In contrast, either the pump 256, or the valve 258, will typically be controlled proportionally. Thus, the output 122 of the pump 256 being directed into the centrifuge 12 may be controlled by any suitable mechanism, whether or not a valve 258 is involved. The pump 256 may completely control that flow rate. The purposes of such adjustment 238 of the influent stream 122 into the centrifuge 12 has been described hereinabove. The diverter valve 264 is a shutdown, primarily, open to a sales line 266 so long as the flow 260 remains within the specified quality. Again, maintaining oil dehydration quality, monitoring it, and so forth are described in detail with respect to FIG. 19.

The tests 234, 236 may fail to provide options for continuing the process 210 of FIG. 19, then the shutoff valve 264 may be activated in order to stop 232 the withdrawal and delivery of oil 170 to the sales line 266. The system 10 permits only oil within specification to go out for sale at the market price and verified to be at the market specified quality.

Once the diverter valve 264 shuts off delivery into the sales line 266, any remaining material 180 must be diverted into the return line 268 for further processing. That processing may involve return to the same tank 162, from which it originated, but will typically be to another. The quality is so poor that it cannot be salvaged to market quality by this system.

Notwithstanding the heavy species flow 262 (e.g., water or brine) may have been separated from the mix 180, it may contain residual traces of oil according to the operational parameters of the centrifuge 12, as described hereinabove, and in the references incorporated herein by reference. Accordingly, the heavy species flow 262 may also move on toward further processing. In fact, those processes may have their own controls, additional centrifuges 12, or the like, depending on economy and other driving parameters.

Meanwhile, the control lines 270a, 270b, 270c, and 270d through which the BS&W meter 193 influences the diverter valve 264, and one or more of the pump 256 and flow control valve 258, may carry more or less data, power, or both. For example, the BS&W meter 193 as illustrated may simply send a report or a signal of a status or a value, such as a voltage. In such a circumstance, the valve 264, the pump 256, and the valve 258 must have their own power, operating several mechanisms, and so forth.

It is possible to have amplifiers power switches, and the like in the lines 270a, in order that the BS&W meter 193 deal only with data and the valves 264, 258 and pump 256 deal only with power. However, this is a matter within the skill of one having ordinary skill Whether motors (e.g., drive motors) or other mechanisms are a part of the BS&W meter 193 is an engineering choice. Data and power are delivered to their respective components 256, 258, 264 being controlled.

With respect to FIG. 21, one will see that a loop or a controller 129 may maintain a matching of settling distances in accordance with certain aspects of the invention. Meanwhile, the BS&W meter 192 may be used as the source of control to literally optimize the operation of the centrifuge 12. One may obtain a maximum or optimize the quantity of the mixture 180 that may be turned out as in-spec flow 260.

As a practical matter, seeing that the controller 129 and comparator 138 operate to control the same centrifuge 12 as does the BS&W meter 193, incompatible interaction is to be avoided. However, the frequency response of the valves 258, 264, and the pump 256 in response to the BS&W meter 193 are comparatively slow frequency, having comparatively long time constants for operation in response to inputs. Meanwhile, with the speed of the centrifuge 12 is comparatively faster. A substantially instantaneous response (comparatively very short time constant) of the controller 129 to variations in pressure differential between the lines 124, 126 assures that the responses of the two controllers 129, 193 are virtually uncoupled.

A system and process in accordance with the invention provide numerous advantages. In fact, the available speed itself with which a centrifuge 12 in accordance with the invention can separate the light species flow 260 from the heavy species flow 262 drives the need for the multiple controls 129, 193.

For example, conventional tank farms or separation facilities may provide weeks, a month, or more time for gravity separation processes and drawing off saleable oil from various tanks 162. In a system and method in accordance with the invention, the centrifuge 12 can process so much greater volume per day, that the demands for real estate, tanks, and labor are all reduced.

For example, in actual operation, typical capacities of 1,000 barrels per eight hour shift are possible through a centrifuge 12 in accordance with the invention. Comparatively, a conventional system of settling tanks may take about a month to process the same amount of oil. That month involves real estate, tanks, and labor to monitor, fill, drain, and otherwise manage and maintain the process.

Another consequence of the speed or performance of a system 10 in accordance with the invention is a burden and benefit. For example, if a process is occurring over dozens or hundreds of acres of facility, in hundreds or thousands of tanks, or dozens of days, the difficulties, logistics, failures, probabilities of error, and the like will differ, as will the consequences.

Just as a system 10 in accordance with the invention may process 1,000 barrels per day of oil, permitting such a system 10 to run "open loop" without precise, immediate, high-frequency response, control systems will render many of the gains mute, due to frequent operation out of specified ranges of control parameters. By providing the feedback control instantaneously to the controller 129 one may maintain the radius of the dispersion band 150. The operation of the centrifugation process or the centrifuge 12 will continue as designed.

Meanwhile, by providing an in line BS&W meter 193, multiple tanks of random qualities may arrive and be processed with instantaneous response, while still obtaining optimization of the maximum output 260 of the centrifuge 12. The maximum percentage 206 of oil 170 from a tank 162, all within specification, is now an obtainable objective.

The system 10 is uncoupled from the normal dependence on the source. Gone is the controlling influences by incoming quality, environmental conditions such as temperature, humidity, and so forth. Gone is the delay causing degradation by microbial effect or the simple operation of internal chemistry of constituents, and so forth.

A system 10 in accordance with the invention provides a new mechanism for quality assurance. For example, if the output 260 to a sales tank 162 results from the process 210, quality is assured on at least two counts. First of all, every barrel of oil 270 placed into a sales tank 162a meets the specification when so delivered thereto 162a. Out of the process 210 and the centrifuge 12 it was processed by this system after extraction from a slop oil 162b and nothing exits that is not then within specification. This is true of every barrel when placed in the tank 162a.

Moreover, the centrifuge 12 operates at approximately 1,000 g or 1,000 times the acceleration of gravity. When oil 170 is placed into a sales tank 162a by itself, having just been centrifuged at 1,000 g's, the single g value available from natural gravity cannot be expected to separate significantly over any consequent month or more. Standing time is actually matter of a few days at a maximum. Such a sales tank 162a will not remain in storage prior to delivery to a refinery for time sufficient to alter its quality.

Every barrel of oil was within specification when placed in the tank 162a. Therefore the average is must be within the specification. The specification can always be met thereafter. Meanwhile, after the centrifugation of the material 180 or mixture 180 to provide specification-pure oil 170, no forces again exist like those in the centrifuge 12, No further separation is possible at any appreciable rate in any of the oil 170 in the sales tank 162. Thus, a mechanism for providing the oil 170, certifying its quality, in view of its specification, and maintaining it at that quality indefinitely, provide a system and method never before attainable.

In accordance with a process and system in accordance with the invention, quality may be predictable, may be created to match virtually any specification, may be maintained over time, may be sealed up in a tank certified to be assured. That is, if no access to the tank is provided, then the quality may be assured with a certification stamp, link, witness mark, seal, or the like.

Similarly, a system and process in accordance with the invention provide additional financial benefits. For example, the practicalities of moving waste liquids 262, as well as sales oil 170 as an output 260 involves testing, verification, loading into trucks, and unloading from trucks. Current processes for testing, verification, and certification of quality take time. Excessive time.

For example, a truck that may cost $100 per hour may spend one hour in loading and one hour in unloading basically while conventional testing is done for the quality of the oil. Meanwhile, any failure to meet quality may result in rejection of the load, or cessation of pumping in response to the quality dropping below a specified level.

In a system and method in accordance with the invention, any testing in accordance with the invention is effectively permanent, need not be repeated, and is so fast, that is actually done in line and online during the process of filling a tank. Accordingly, a truck may load and unload with a certification ticket that originates with the processing plant 10, which certification may continue all the way through to a refinery. The hours, time, certainty, and risks are all improved in accordance therewith.

The present invention may be embodied in other specific forms without departing from its purposes, functions, structures, or operational characteristics. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed and desired to be secured by United States Letters Patent is:

1. A method comprising:
   providing a tank comprising walls and a floor;
   providing a mixture, effectively inseparable by the influence of gravity in a commercially reasonable time;
   filling the tank from the floor to a liquid level thereabove with a fixed volume of the mixture to be drained therefrom at a later time, leaving an overlayer thereabove comprising a gaseous composition;
   thief-sampling the mixture by extracting a sample as a single volume of the mixture drawn exclusively from proximate a surface representing the liquid level in the tank;
   separating the sample into at least three layers;
   measuring a light fraction of the sample constituting a light component, a heavy fraction of the sample constituting a heavy component, and a solid fraction of the sample constituting a solid component, based on the contents corresponding to the at least three layers; and
   calibrating a BS&W sensor detecting the heavy component in a flow drawn before operation of a centrifuge operably connected between the tank and the BS&W sensor, the flow taken from proximate the liquid level and unseparated, based on the heavy fraction; and
   controlling the flow from the tank into the centrifuge, during its operation as a separator, based on a residual amount of the heavy component remaining in the light component downstream from the centrifuge as detected by the BS&W sensor thereat.

2. The method of claim 1, comprising:
   providing an exit line operably connected downstream from the tank and containing a control device constituted by at least one of a pump and a valve; and
   providing a controller operably connected to receive an input signal from the BS&W sensor downstream of the tank and control the flow by adjusting the control device in response thereto.

3. The method of claim 1, further comprising:
   providing a specification designating a maximum fraction of at least one of the heavy component and the solid component permitted to remain in an output flow comprising the light component separated by the centrifuge and exiting therefrom; and
   controlling the flow into the centrifuge, based on detection, by the BS&W meter of a flow fraction of at least one of the heavy component and the solid component with respect to the maximum fraction.

4. The method of claim 3, further comprising:
   measuring, by the BS&W sensor, a heavy fraction of the mixture in the outlet line;
   determining a minimum value of the flow permissible to pass from the tank into the centrifuge while remaining operational; and
   diverting the output flow back to the tank in response to the flow approaching the minimum value.

5. The method of claim 4, further comprising:
   closing the tank against receiving more of the mixture;
   mixing the mixture for a first period of time; and
   resting the mixture by leaving it quiescent in the tank for a second period of time.

6. The method of claim 5, further comprising:
   providing a snorkel operably connected to the exit line positioned proximate a bottom surface of the tank to draw the mixture from the tank proximate the liquid level;
   operating the snorkel to automatically remain at a constant position with respect to the liquid level as the liquid level decreases toward the floor; and
   adjusting the flow as the liquid level decreases.

7. The method of claim 1, further comprising:
   providing a flow control automatically controlling the flow based on the heavy fraction corresponding to a parameter having a value detected by the BS&W sensor.

8. The method of claim 1, further comprising:
   determining a minimum flow of the lighter component permissible with the pump and the centrifuge remaining operational;
   adjusting the flow based on the BS&W sensor;
   diverting the light component downstream from the centrifuge into the tank; and
   halting the flow when the value corresponds to approaching the minimum flow.

9. The method of claim 1, wherein the mixture contains substantially all of the components distributed throughout substantially all regions between the liquid level and the floor.

10. The method of claim 9, wherein
    the components include oil, water, and solids, and the gaseous composition comprises air and constituents of a vapor phase of the oil; and
    the portion of the mixture is inseparable, due, at least in part, to a dwell time within the tank inadequate for gravitational separation thereof.

11. The method of claim 10, wherein the components are distributed among one another over ranges comprising:
    solids ranging from about zero percent near the liquid level to about less than 3 percent near the floor;
    water ranging from about zero percent near the liquid level to about less than 15 percent near the floor; and oil ranging from about 100 percent near the liquid level to about 90 percent near the floor.

12. The method of claim 11, wherein the solids range from about zero near the liquid level to about one percent near the floor, and the water ranges from about zero percent near the liquid level to about five percent proximate the floor.

13. A method comprising:
providing a tank comprising walls and a floor;
providing a mixture comprising components effectively inseparable by the influence of gravity;
filling the tank with a fixed quantity of the mixture, comprising a liquid, from the floor to a liquid level thereabove, the liquid level sharing a boundary with an overlayer thereabove comprising a gaseous composition;
sampling the mixture by extracting a single, fixed volume as a sample thereof exclusively from a location proximate the liquid level in the tank;
separating the sample into the components by centrifuging;
measuring a light fraction constituting a light component separated in the sample, a heavy fraction constituting a heavy component separated in the sample, and a solid fraction constituting a solid component separated in the sample;
providing a separator, connected to drain the tank directly from proximate the liquid level; provided with a light outlet and a heavy outlet for the light component and heavy component, respectively, following separation by the separator, and capable of separating the components faster than the influence of gravity;
draining a flow, unseparated, from the tank past a BS&W sensor in the light outlet;
calibrating the BS&W sensor to automatically detect the heavy component remaining in the light component, based on relative fractions of the heavy component and light component determined from the measuring; and
controlling the flow based on an output of the BS&W sensor during operation of the separator.

14. The method of claim 13, comprising:
providing a controller operably connected to receive an input signal from the BS&W sensor and control the flow in response thereto;
providing a specification designating a maximum fraction of at least one of the heavy component and the solid component; and
diverting the light output into the tank when the flow, corresponding to the input signal from the BS&W sensor would render the separator inoperable.

15. A method comprising:
providing a tank comprising a floor at a bottom thereof, a top, and walls extending therebetween and containing a mixture comprising a light component, heavy component, and sediment component effectively inseparable by the influence of gravity in a commercially reasonable time;
thiefing a single sample of fixed volume of the mixture by extracting exclusively proximate a liquid surface proximate the top;
determining a light fraction, heavy fraction, and sediment fraction by centrifuging the sample to separate the amounts of the light component, heavy component, and sediment component, respectively, contained therein;
calibrating, based on the heavy fraction, a BS&W sensor by exposing the BS&W sensor to a flow of the mixture drawn from proximate the liquid surface and unseparated;
separating the flow into the light component and heavy component by controlling the flow into a centrifuge based on a residual amount of the heavy component detected by the BS&W sensor in a light component output from the centrifuge.

16. The method of claim 15, comprising:
reducing the flow into the centrifuge in response to an output from the BS&W sensor corresponding to a specified content of the heavy component detected thereby in the light component output.

17. The method of claim 16, comprising:
providing an exit line operably connected downstream from the tank and containing at least one of a pump and a valve; and
providing a controller operably connected to receive an input signal from the BS&W meter connected to the light component output downstream of the centrifuge and control the at least one of a pump and a valve in response thereto.

18. The method of claim 1, further comprising:
providing a specification designating a maximum fraction of at least one of the heavy component and the solid component;
controlling the light component output to remain within the specification, by controlling the flow into the centrifuge.

19. The method of claim 18 comprising:
determining minimum value of the flow permissible, based on operational characteristics of the centrifuge and the at least one of a pump and a valve; and
diverting the light component output from the centrifuge into the tank when the BS&W sensor corresponds to the flow falling below the minimum value.

* * * * *